(12) United States Patent
Babic et al.

(10) Patent No.: US 10,172,744 B2
(45) Date of Patent: Jan. 8, 2019

(54) COMPRESSION DEVICE

(71) Applicant: 3M INNOVATIVE PROPERTIES COMPANY, Saint Paul, MN (US)

(72) Inventors: Ivana Babic, Milan (IT); Guido Hitschmann, Neuss (DE); Edward L. Weaver, II, Milford, OH (US); Federico Casotto, Bologna (IT); Pasquale Cirulli, Milan (IT); Andrea Daelli, Milan (IT)

(73) Assignee: 3M Innovative Properties Company, Saint Paul, MN (US)

( * ) Notice: Subject to any disclaimer, the term of this patent is extended or adjusted under 35 U.S.C. 154(b) by 266 days.

(21) Appl. No.: 14/762,496

(22) PCT Filed: Jan. 16, 2014

(86) PCT No.: PCT/US2014/011857
§ 371 (c)(1),
(2) Date: Jul. 22, 2015

(87) PCT Pub. No.: WO2014/116497
PCT Pub. Date: Jul. 31, 2014

(65) Prior Publication Data
US 2016/0008178 A1    Jan. 14, 2016

(30) Foreign Application Priority Data

Jan. 25, 2013 (GB) .................................. 1301309.9
Apr. 30, 2013 (GB) .................................. 1307718.5

(51) Int. Cl.
*A61F 13/08* (2006.01)

(52) U.S. Cl.
CPC ............ *A61F 13/08* (2013.01); *A61F 13/085* (2013.01)

(58) Field of Classification Search
CPC ...... A61F 5/0106; A61F 13/08; A61F 5/0109; A61F 13/107; A61F 13/061;
(Continued)

(56) References Cited

U.S. PATENT DOCUMENTS

| 3,538,194 A | 11/1970 | Barrett |
| 4,206,751 A | 6/1980 | Schneider |

(Continued)

FOREIGN PATENT DOCUMENTS

| CN | 2638458 Y | 9/2004 |
| CN | 101677877 A | 3/2010 |

(Continued)

OTHER PUBLICATIONS

Encircle® Compression Therapy. Web. Apr. 23, 2012. <http://www.encirclemedical.com>.

(Continued)

*Primary Examiner* — Ophelia A Hawthorne
(74) *Attorney, Agent, or Firm* — 3M Innovative Properties Company; Trisha D. Adamson

(57) ABSTRACT

A compression device for applying compression to a body part of a user. The compression device comprises a sleeve for substantially covering a portion of the body part of a user. The sleeve has an upper edge, a lower edge and an opening extending from its upper edge to its lower edge, said opening having two side edges. The first side edge is provided with one half of a zipper and the second side edge is provided with a complementary half of said zipper. The sleeve includes at least one expandable gusset provided with a releasable closure system extending along the length of said gusset, said gusset and releasable closure system being configured and arranged, such that when said releasable closure system is closed said gusset is prevented from (Continued)

expansion and when said releasable closure system is opened said gusset is allowed to expand.

16 Claims, 16 Drawing Sheets

(58) Field of Classification Search
CPC ...... A61F 13/085; A61F 13/062; A61F 13/06; A61F 5/0111; A61F 5/0104; A61F 13/00038; Y10S 128/15
See application file for complete search history.

(56) References Cited

U.S. PATENT DOCUMENTS

| | | |
|---|---|---|
| 5,653,244 A | 8/1997 | Shaw |
| 7,037,282 B2 | 5/2006 | Coleman |
| 8,118,762 B2 | 2/2012 | Bort |
| 8,469,914 B2 * | 6/2013 | Allard .................. A61F 13/085 602/62 |
| 2002/0062096 A1 | 5/2002 | Bennett |
| 2003/0195449 A1 | 10/2003 | Coleman |
| 2006/0004315 A1 * | 1/2006 | Bort ...................... A61F 5/0109 602/62 |

FOREIGN PATENT DOCUMENTS

| | | |
|---|---|---|
| CN | 101849714 A | 10/2010 |
| CN | 201830967 U | 5/2011 |
| CN | 202618379 U | 12/2012 |
| DE | 202004010779 | 2/2012 |
| EP | 1974704 | 10/2008 |
| EP | 1974704 | 5/2010 |
| WO | WO 2006-048619 | 5/2006 |

OTHER PUBLICATIONS

International Search Report for PCT International Application No. PCT/US2014/011857, dated Apr. 17, 2014, 3 pages.
Supplementary Search Report for Chinese Application No. 201480006014.2.

* cited by examiner

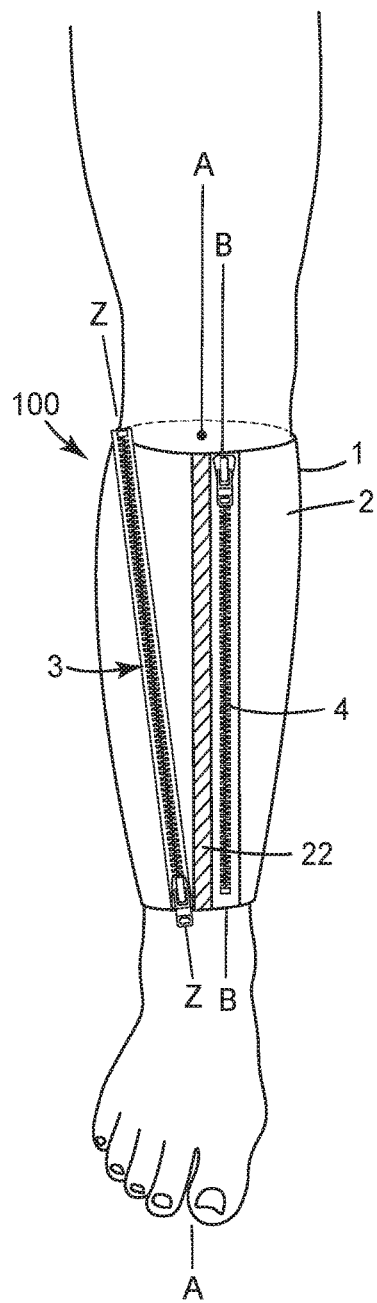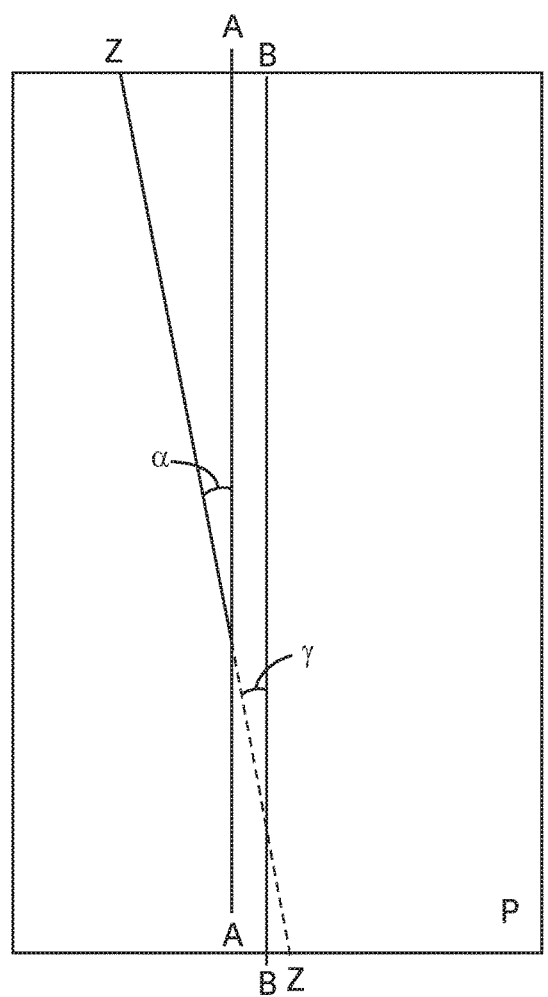
FIG. 6a
FIG. 6b

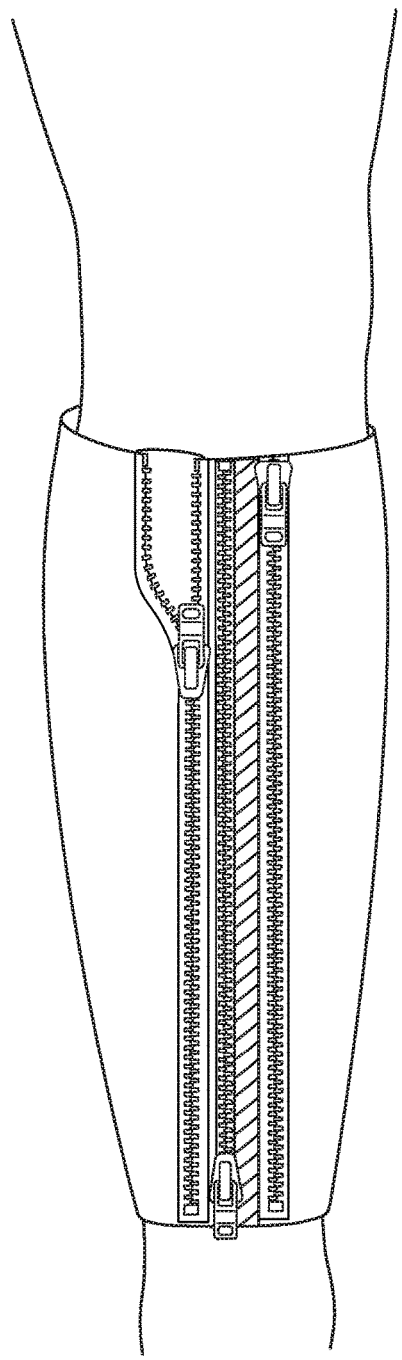
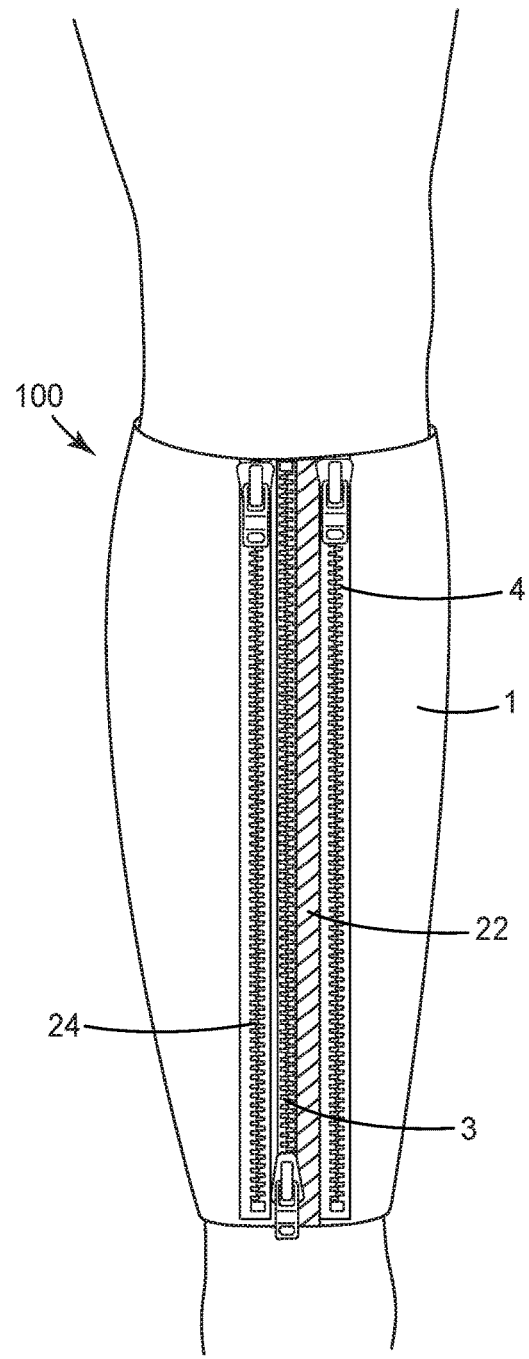
FIG. 14c
FIG. 14d

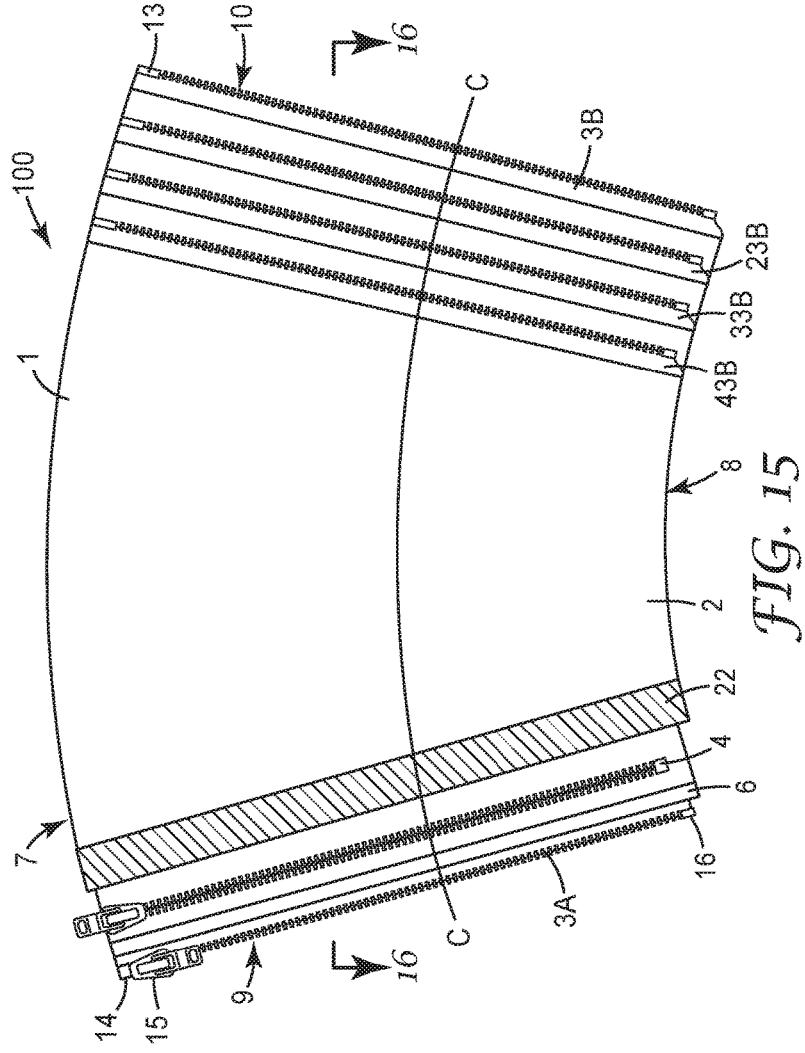
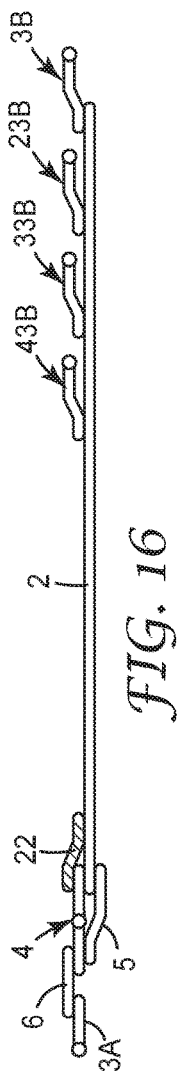

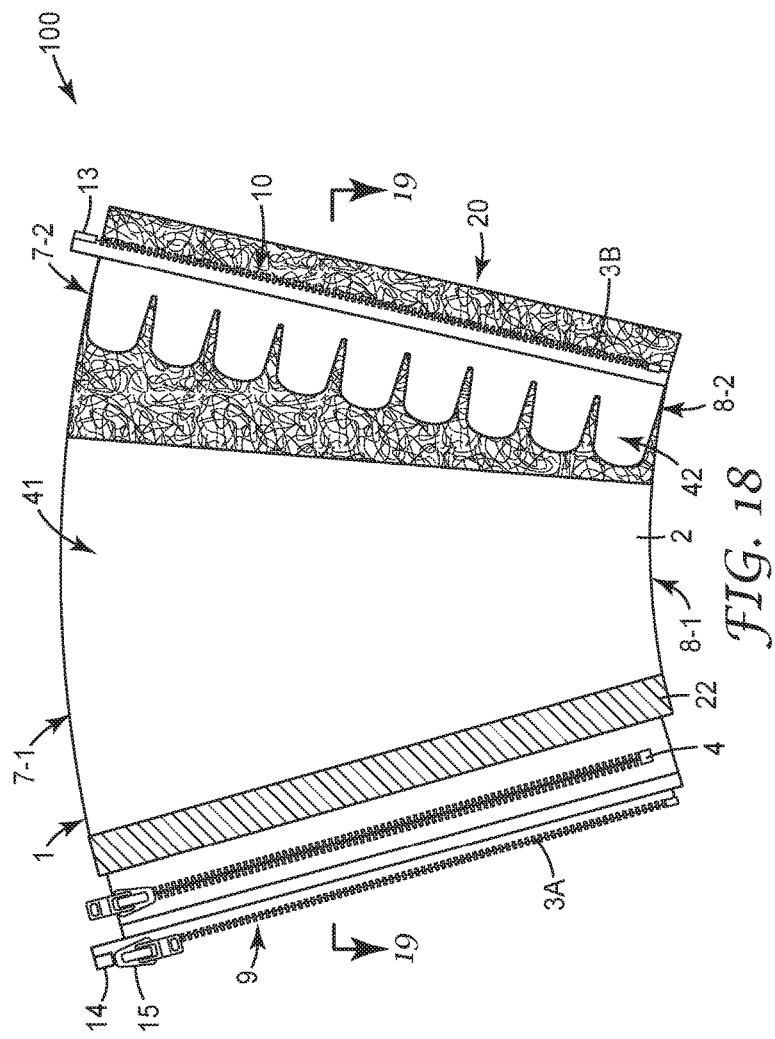
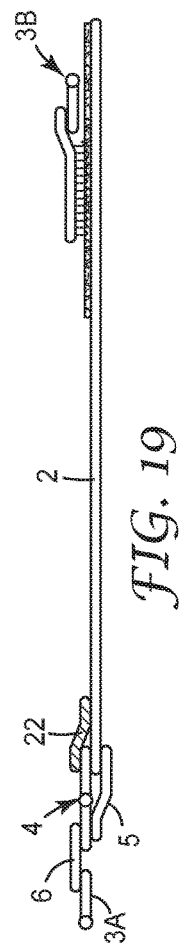

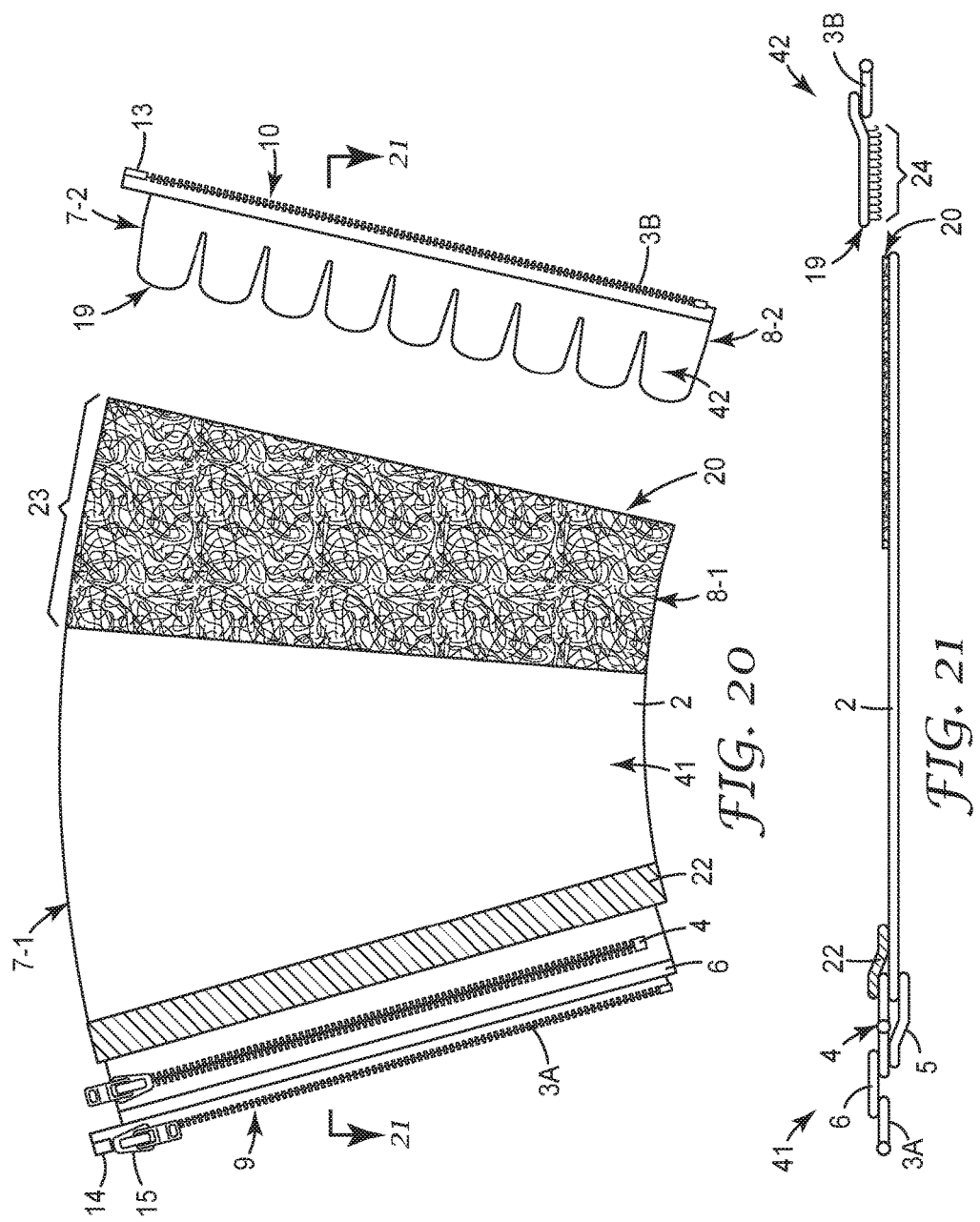

COMPRESSION DEVICE

CROSS REFERENCE TO RELATED APPLICATIONS

This application is a national stage filing under 35 U.S.C. 371 of PCT/US2014/011857, filed Jan. 16, 2014, which claims priority to Great Britain Application No. 1307718.5, filed Apr. 30, 2013 and Great Britain Application No. 1301309.9, filed Jan. 25, 2013, the disclosures of which are incorporated by reference in their entirety herein.

FIELD

The present invention relates to compression devices, in particular compression devices for applying compression to a body part (e.g. a limb, torso, neck or head or neck/head combination) of a user for the use in the treatment and/or management of oedema and other venous and lymphatic disorders of a body part (e.g. limb, torso, neck or head), more particularly venous leg ulcers and lymphoedema of a limb.

BACKGROUND

Compression therapy is generally prescribed to support an insufficient venous or lymphatic system in returning blood or lymph to the heart. Accordingly compression is generally considered to be the standard treatment for use in the treatment of oedema and other venous and lymphatic disorders e.g. of the lower limbs venous leg ulcers and other clinical conditions, such as lymphoedema. The positive effects of compression therapy on venous lymph return, as well as on the healing of chronic venous (leg) ulcers, are well documented in the medical literature.

Compression bandages and stockings are the most common compression systems used for compression therapy. Compression stockings however often do not provide the desired therapeutic compressive pressure.

Other compression systems have been proposed. A number of these can be generically described as to include a sleeve-like garment to be wrapped around a limb and a closure mechanism, e.g. a zipper, to secure the sleeve-like garment around the limb (e.g. see U.S. Pat. No. 3,538,194, U.S. Pat. No. 5,653,244, US 2002/0062096, US 2003/195449, WO 2006/048619). EP 1 974 704 discloses a compression device for providing compression on a body part characterized by a main part for substantially covering a main portion of the body part, and a tongue attachable to the main part for completing the circumference around the body part, wherein the main part at each edge is provided with fastening means attachable to the tongue, in particular wherein the main part at each edge is provided with one half of a zip fastener, and the tongue is provided with a number of halves of the zip fastener mating with the half provided on the main part.

ENCIRCLE Medical Device Linkedin Group markets two layer compression stockings including (Class 1 and 2) knee-high outer stocking worn over top of an inner (Class A) knee-high stocking, where the outer stockings having a zipper extending from the top down to about mid-calf and where it is described the zipper can be opened to release pressure and closed to increase support.

SUMMARY OF INVENTION

While zippers are appealing as a closure mechanism for compression devices including a sleeve-like garment (referred to in the following simply as "sleeve") to be wrapped around a body part (e.g. a limb), they have been found not well-suited for such compression systems, in particular those providing high levels of compression, since they can be very difficult or even impossible to close under tension.

Surprisingly it has been found that by providing such a sleeve that is to be opened and closed with a zipper, with at least one expandable gusset provided with a releasable closure system (e.g. a secondary zipper) extending along its length, such that when releasable closure system is closed said gusset is prevented from expansion and when said releasable closure system is opened said gusset is allowed to expand between the complementary halves of the releasable closure system so as to allow for an expansion of the width of the sleeve, it is possible to significantly decrease the force necessary to close the main zipper and in turn the force needed to apply a compression device such a sleeve onto a body part (e.g. a limb, torso, neck, head or portions thereof and/or, if applicable, combinations thereof (for example a portion of neck and head in combination)) of a user.

Accordingly, in one aspect of the invention there is provided a compression device for applying compression to a body part of a user comprising a sleeve for substantially covering a portion of the body part of a user, wherein the sleeve has an upper edge, a lower edge and an opening extending from its upper edge to its lower edge, said opening having two side edges, wherein the first side edge is provided with one half of a zipper and the second side edge is provided with a complementary half of said zipper, wherein the sleeve includes at least one expandable gusset provided with a releasable closure system extending along the length of said gusset, said gusset and releasable closure system being configured and arranged, such that when said releasable closure system is closed said gusset is prevented from expansion and when said releasable closure system is opened said gusset is allowed to expand between the opened parts of the releasable closure system so as to allow for an expansion of the width of the sleeve.

Desirably, the at least one expandable gusset extends substantially lengthwise between the upper and lower edges of the sleeve.

Compression devices described herein, in particular sleeves thereof, are particularly suited for covering a portion of a limb, a portion of the torso, a portion of the neck, a portion of a head or a portion of a neck and head in combination of a user e.g. for the use in the treatment and/or management of oedema.

When the compression device is in use on the respective body part of the user (such as a limb of the user or the torso or neck of the user), desirably the sleeve is disposed about a central axis (A), said central axis lying in a plane (P). In such embodiments, when the compression device is in use on the body part of the user and the zipper and the releasable closure system are closed, the releasable closure system extends along a second axis (B), wherein relative to a projection of the second axis onto said plane (P) containing the central axis (A), it is favorable that this second axis is either in parallel alignment or inclined forming an acute angle ($\beta$) up to 45° inclusive relative to the central axis. More favorably this acute angle ($\beta$) may be equal to or less than 35°, even more favorably equal to or less than 30°, yet even more favorably equal to or less than 25°, most favorably equal to or less than 20°. Alternatively or in addition, for such embodiments (where the sleeve is desirably disposed about a central axis (A), said central axis lying in a plane (P)), when the compression device is in use on the body part of the user and the zipper and the releasable closure system are closed, the zipper extends along a third axis (Z), wherein relative to a projection of the third axis onto said plane (P) containing the central axis (A), it is favorable that this third axis is either in parallel alignment or inclined forming an acute angle (α) up to 45° inclusive relative to the central axis. More favorably this acute angle (α) may be equal to or less than 35°, even more favorably equal to or less than 30°, yet even more favorably equal to or less than 25°, most favorably equal to or less than 20°. For such embodiments in which said releasable closure system extends along a second axis (B) and the zipper extends along a third axis (Z) when the compression device is in use on the body part of the user and the zipper and the releasable closure system are closed, it is desirable that the second axis (B) and third axis (Z) are parallel to one another or inclined to one another such that the angle formed at a theoretical point of intersection between the second and third axes is equal to or less than 30°.

It will be appreciated that compression devices described herein for use on a portion of a head of the user or a portion of the neck and head in combination, when the compression device is in use on the respective part of the user, the sleeve may not be disposed about a central axis (A). Moreover compression devices suitable for use with necks and heads will often be used for both, i.e. configured to cover a portion of both the neck and head of the user. Such devices may be configured for example like a fitted hood covering the neck, chin and over the head leaving the face free where the zipper and the releasable closure system may be provided either along the top and back of the head or along the front down the chin/jaw and front of the neck. For such embodiments, desirably the axes along which the zipper and the releasable closure system run are desirably parallel to one another or substantially parallel to one another (i.e. inclined to one another such that the angle formed at a theoretical point of intersection between the axes is equal to or less than 5°).

It has been found favorable to configure and arrange the at least one gusset and its associated releasable closure system such that a half of the releasable closure system extends along one long side edge of the gusset and a second complementary half of the releasable closure system extends along the other long side edge of the gusset.

The at least one gusset may be substantially rectangular in shape (in particular in form a band); triangular in shape; diamond-shaped (in particular elongated diamond shaped); canoe-shaped or rowboat-shaped. Canoe-shaped is to be understood to mean that gusset shows two long, bowing sides meeting together to each end forming a point, whereas rowboat-shaped is to be understood to mean that the gusset shows two long, bowing sides meeting together at one end to form a point while the other ends of the bowing sides are joined by a transverse side.

Advantageously the compression device sleeve is configured and arranged such that, in use, when the releasable closure system is opened, said gusset can expand to a width up to and including 50 mm (in particular up to and including 35 mm, more particularly up to and including 20 mm) in addition to that width that the gusset has when releasable closure system is closed.

Desirably the at least one gusset is made of a material having elasticity in at least the transverse direction of the sleeve. For the sake of clarity, it is to be appreciated that after application of a compression device onto a body part (e.g. limb, torso, neck or head or neck/head combination) of a user, the transverse direction of the sleeve will also be a circumferential direction. In accordance with ASTM D4848-98 (2012) and BS EN 14704-1:2005 elasticity is that property of a material by virtue of which it tends to recover its original size and shape immediately after removal of the force causing deformation. To further facilitate desirable functionality of the gusset in regard to closing the main zipper and in turn the force needed to apply a compression device such a sleeve onto the body part (e.g. a limb, torso, neck or head or neck/head combination) of user, the at least one gusset may be favorably made of a material that exhibits at 30% elongation in said transverse direction a tension equal to or greater than 0.02 N per mm width of material (e.g. as measured according to BS EN 14704-1:2005 as described in detail below), preferably a tension equal to or greater than 0.05 N per mm width of material at 30% elongation. Also to further facilitate desirable functionality of the gusset in regard to closing the main zipper and in turn the force needed to apply a compression device such a sleeve onto the body part (e.g. a limb, torso, neck or head or neck/head combination) of user, the at least one gusset may be favorably made of a material that exhibits at 10% elongation in said transverse direction a tension equal to or less than 0.5 N per mm width of material, preferably equal to or less than 0.3 N per mm. (e.g. as measured according to BS EN 14704-1:2005 as described in detail below).

The at least one gusset may be made of a material that does not have elasticity in at least the transverse direction of the sleeve. Here it is desirable that the gusset and its associated releasable closure system are configured and arranged such that when the releasable closure system is closed the gusset folds up behind the releasable closure system and when the releasable closure system is opened, said gusset can unfold between the opened parts the releasable closure system.

Favorably the at least one gusset extends a height that is equal to or greater than 40% (in particular equal to or greater than 50%, more particularly equal to or greater than 60%, most particular equal to or greater than 70%) of the height of the sleeve from the upper to lower edge. More favorably within these mentioned ranges the at least one gusset may extend a height that is equal to or less than 100% of the height of the sleeve from the upper to lower edge.

For convenience in use, it is desirable that the zipper opening and closing the sleeve and/or the gusset-associated releasable closure system are accessible for actuation from the outside of the sleeve. Favorably the zipper opening and closing the sleeve is a separating-type zipper. When the zipper is opened, desirably the sleeve is substantially rectangular, trapezoidal, or irregular in shape. When the zipper is closed the sleeve is substantially cylindrical, barrel or truncated-conical in shape.

The sleeve may include two or more expandable gussets, each provided with its own releasable closure system.

Advantageously, the gusset-associated releasable closure system is a zipper, in particular a non-separating type zipper.

The term "zipper" as used herein includes mechanical closure devices comprising two zipper-tape halves, each provided teeth or other elements including (e.g. male and/or female) interlocking profiles, which can interlocked together or disengaged from another via the use of a slider to form a closed or opened zipper chain, respectively. An example of a toothless zipper includes the closure system marketed by GORE under the trade designation LOCKOUT which includes a slider that interlocks the two double channeled polymer tracks.

Another aspect of the present invention is a method of applying compression devices described herein onto the body part (e.g. limb, torso, neck, head or neck/head combination) on a user, said method comprising the steps of:

a) opening the sleeve by opening the zipper and opening the at least one expandable gusset by opening its releasable closure system;
b) positioning the sleeve about the body part of the user;
c) closing the zipper; and
d) closing the releasable closure system, whereby if sleeve includes two or more gussets the closure of the releasable closure systems may be performed, as applicable, sequentially or simultaneously.

The above summary of the present invention is not intended to describe each disclosed embodiment or every implementation of the present invention. The description that follows more particularly exemplifies illustrative embodiments. Also further embodiments are described in dependent claims. In several places throughout the application, guidance is provided through lists of examples, which examples can be used individually and in various combinations. In each instance, the recited list serves only as a representative group and should not be interpreted as an exclusive list.

BRIEF DESCRIPTION OF DRAWINGS

The invention will now be described with reference to the accompanying drawings in which:

FIG. 1 represents a top view of an exemplary embodiment of a compression device in accordance with the invention described herein, while

FIG. 4 represents a top view of a second exemplary embodiment of a compression device in accordance with the invention described herein, while

FIG. 6a represents a perspective view of the exemplary embodiment depicted in FIGS. 4 and 5 shown in use on the lower leg of a user. FIG. 6b shows a projection of the axes B and Z (depicted in FIG. 6a) onto a plane P containing the central axis A (that is also depicted in FIG. 6a).

FIG. 9 represents a top view of a further exemplary embodiment of a compression device in accordance to the invention described herein, while

FIG. 15 represents a top view of an exemplary embodiment of a width-adjustable compression device in accordance with the invention described herein, while FIG. 16 shows a cross-sectional view of the exemplary embodiment depicted in FIG. 15.

FIGS. 18 to 21 represent illustrations of a further width-adjustable exemplary compression device in accordance to the invention described herein, where FIGS. 18 and 20 provide top views of the exemplary embodiment in two configurations and FIGS. 19 and 21 provide cross-sectional views of the exemplary embodiment in the said two configurations.

In the description that follows, terms such as 'top', 'bottom', 'above', 'below', etc, refer only to features as shown in the Figures, and unless expressly stated otherwise, no restriction as to orientation of use, etc, is intended. Not all Figures are to the same scale.

DETAILED DESCRIPTION

It is to be understood that the present invention covers all combinations of particular, suitable, desirable, favorable, advantageous and preferred aspects of the invention described herein.

Figure 1:
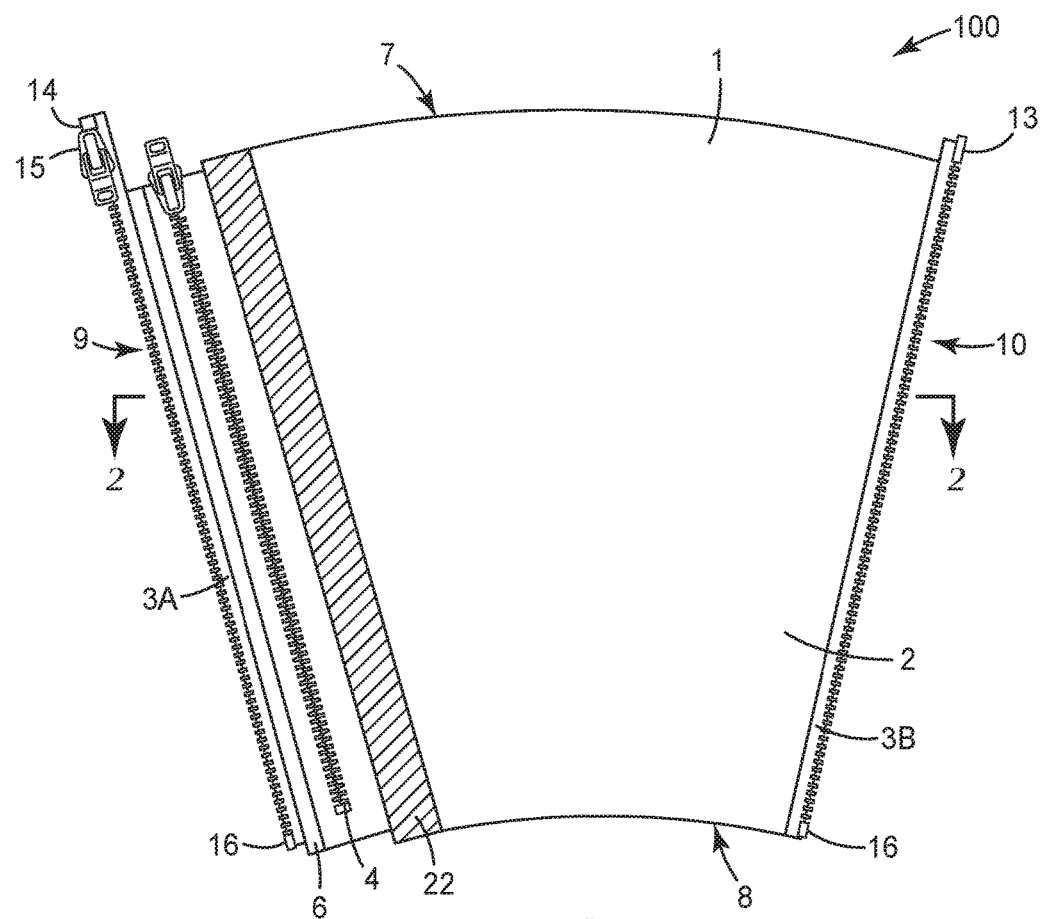
Figure 2:
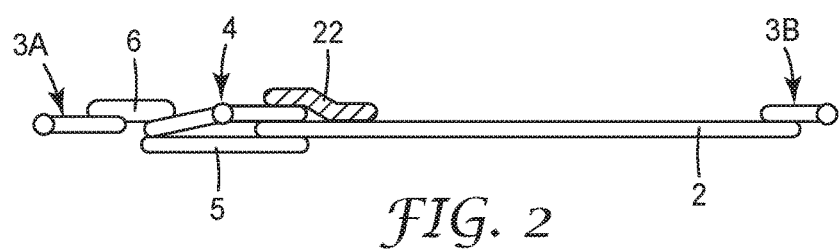
FIG. 2 shows a cross-sectional view of the exemplary embodiment depicted in FIG. 1.

FIG. 1 shows a top view of the exterior of an exemplary embodiment of a compression device (100) for use in apply compression to a body part, in particular a limb of a user, while FIG. 2 shows a cross-sectional view of this exemplary embodiment. The device comprises a sleeve (1) for substantially covering a portion of the body part, in particular a portion of the limb, of a user. The sleeve includes an upper edge (7) and a lower edge (8). When the device is in use on the limb, typically the upper edge is located towards to the torso of the user and the lower edge distant to the torso of the user, and both upper and lower edges, being essentially transverse, will be located essentially circumferentially around the limb after application. As can be appreciated from FIG. 1, the sleeve includes an opening extending from its upper edge to its lower edge, the opening having two side edges (9, 10). The first side edge (9) is provided with one half of a zipper (3A), including a slider (15) and box (14) and the second side edge (3B) is provided with a complementary half of the zipper (3B) including an insert pin (13). Each half of the zipper includes a stop (16).

The zipper with its two complementary halves allows the user or a care-giver to open and close the sleeve, and this zipper is generally referred to herein as the main zipper. As can be appreciated from the exemplary embodiment depicted in FIGS. 1 and 2 and FIG. 3 showing the exemplary embodiment on the limb of a user, once positioned onto the limb of the user, when then the main zipper is closed, the compression device, in particular the sleeve advantageously completely encircles the relevant portion of the limb (in this particular case the lower leg of the user) and a main part (2) of the sleeve will almost encircle the limb.

For compression devices suitable for use with the lower leg of the user, favorably the sleeve is configured and arranged such that in use the main zipper will generally be positioned towards the front, in particular so that the main zipper extends generally along the tibia. Accordingly for such embodiments the main part of the sleeve will typically be positioned around the back and sides of the lower leg, in particular next to the calf muscles.

The sleeve, in particular the main part of the sleeve, favorably comprises a material that is suitable for use in applying compression. Such materials are known in the art.

Favorably such materials have low flexural rigidity and are stretchable, so that they can readily adapt to the shape of the relevant body part (e.g. limb, torso, neck, head or neck/head combination), while at the same time not being too easily stretched under tension, so that the desired provision of compression onto the body part (e.g. limb, torso, neck, head or neck/head combination) can be achieved. For comfort in wearing, such materials are desirably breathable.

Sleeves may be provided with one or more stiffeners to facilitate maintenance of sleeve shape, in particular to minimize any tendency towards vertical collapsing or slipping-down of the sleeve, stiffeners may be provided e.g. in the form of wires, bars, grids, or pads having limited width in the transverse direction of the sleeve. In the exemplary embodiment depicted in FIGS. 1 and 2, an elongate stiffener (22) is provided which extends between the upper and lower edges of the sleeve. Stiffeners may be made of e.g. metal or thermoplastic materials including thermoformable thermoplastic materials (such as polypropylene, polyamide, polyester (e.g. 3M Scotchcast Thermoplastic Material 72362)). For stiffeners having a width greater than five millimeters, it may be favorable to provide them with perforations to allow for breathability. For design and/or fixing purposes, stiffeners may be provided within a fabric pocket which is subsequently attached to the appropriate part(s) of the sleeve or alternatively stiffeners may be positioned on the surface of the appropriate part(s) of the sleeve, which are then covered completely with a sheet of fabric that is sewn or laminated onto the respective part(s) of the sleeve.

Although not specifically shown in the exemplary embodiment depicted in FIGS. 1 and 2, compression devices may be configured to include other structural elements. For example, compression devices for use on the lower leg may include a foot portion extending from the sleeve, in particular extending from an appropriate portion of the lower edge of the sleeve. Such a foot portion may be configured and arranged in the form of a stir-up or alternatively such as foot portion may be configured to provide a more extensive covering of the foot. Moreover the sleeve and such a foot portion may be configured and arranged so as to provide a boot-like compression device, either closed or opened toed and/or either closed or opened heeled. Such a foot part may be provided integrally with the sleeve or alternatively as a separate component that can be attached to the sleeve by an appropriate fastening means, such as buttons, mechanical fasteners and the like. Compression devices may also include bladders or gel inserts to facilitate modification of circumferential size. In this regard, sleeves, for example, could be provided with double walls or interior pockets for such inserts so that such insert(s) may be inserted and/or removed as needed or desired.

As can be appreciated from the exemplary embodiment depicted in FIGS. 1 and 2 and the other exemplary embodiments described herein, the main zipper is desirably accessible for actuation from the outside of the sleeve, In addition the main zipper is favorably a separating-type zipper (also called an open end zipper). For ease in opening and closing such a zipper, in particular by the user, generally it is favorable that the insert pin and box of complementary halves of separating-type zipper are located near the upper edge, so that in use the insert pin and box are located towards the torso of the user. This facilitates reaching and handling these parts of the zipper to insert the pin into the box and to initiate the zipping operation, and in addition, the closing operation is facilitated due the downward pulling of the zipper slider towards the stop. Use, in particular insertion of the pin into the box, may be further facilitated by extending the complementary zipper tape halves beyond the upper edge, for example as shown in exemplary embodiment depicted in FIG. 1.

Figure 4:
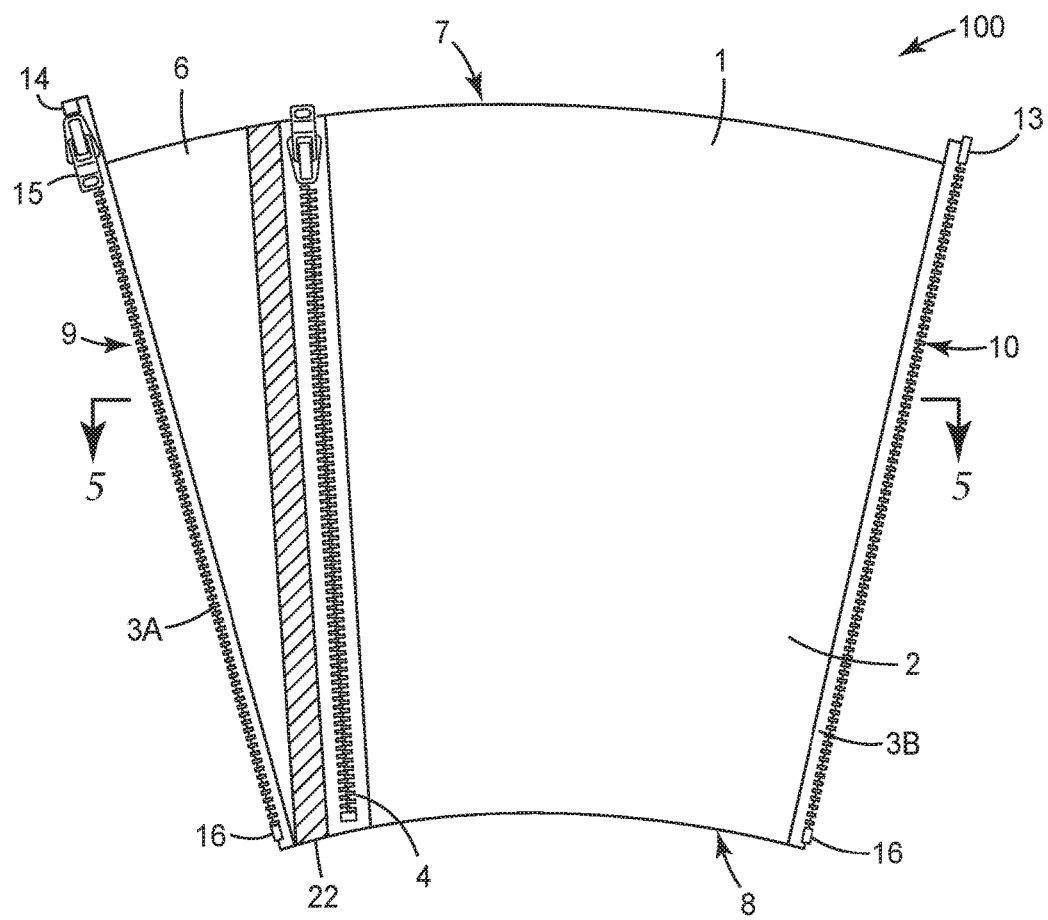
Figure 5:
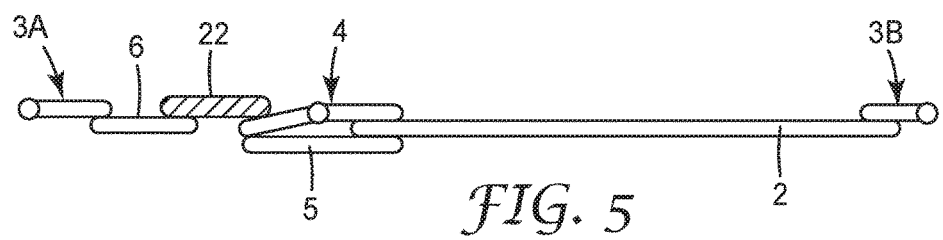
FIG. 5 shows a cross-sectional view of the exemplary embodiment in FIG. 4.

When the main zipper is opened, the sleeve may be substantially trapezoidal in shape (for example, as can be appreciated from the exemplary embodiment depicted in FIG. 1), or alternatively the sleeve may be substantially rectangular or even irregular in shape. In regard to the latter, FIGS. 4 and 5 show top and cross-sectional views, respectively, of a further exemplary embodiment of a compression device which is essentially the same as the exemplary embodiment shown in FIGS. 1 and 2, except that the overall form of the sleeve is irregular (and the position of the optional stiffener (22) is shifted). As will be described in more detail below the result of this difference is that in use of the compression device, when the main zipper is closed, the main zipper will disposed at angle and running to a degree circumferential about the body part, in particular the limb, of the user, which can further facilitate ease in use and opening and closing the main zipper.

For facilitating an optimal fit onto a part of the body part (e.g. onto a part of a limb, the torso, neck, head or neck/head combination) of a user, the upper edge and/or the lower edge of the sleeve may be favorably slightly curved, in particular the upper edge may be slightly convex and/or the lower edge which is normally positioned distant to the torso of the user, may be either slightly concave or convex. Alternatively or in addition thereto, one or both of the side edges (along which the complementary halves of the main zipper run) may be slightly curved, in particular slightly convex. This may be facilitating fitting over well-developed calves. In use, when the main zipper is closed, favorably the sleeve is substantially cylindrical, barrel or truncated-conical in shape. As mentioned above, the sleeve may favorably have the form of a hood for use on the head or on the neck/head of the user in combination.

From FIG. 3 showing the exemplary embodiment depicted in FIGS. 1 and 2 on the limb, i.e. the lower leg, of a user, it can be appreciated that in use the sleeve (1) of this particular exemplary compression device (100) is substantially truncated-conical in shape. Returning to FIGS. 1 and 2, it can be seen that the sleeve of this exemplary embodiment includes an expandable gusset (5; visible in FIG. 2) provided with a releasable closure system (4), in this case a zipper, extending along the length of said gusset. As can be appreciated from FIGS. 1 and 2, the gusset and its associated releasable closure system (4) are configured and arranged, such that when said releasable closure system is closed said gusset is prevented from expansion and when said releasable closure system is opened said gusset is allowed to expand between the opened parts of the releasable closure system so as to allow for an expansion of the width of the sleeve.

As can be appreciated from the exemplary embodiment depicted in FIGS. 1 and 2 and the other exemplary embodiments described herein, the releasable closure systems associated with gussets are desirably accessible for actuation from the outside of the sleeve.

Also indicated above, favorably the gusset(s) and its (their) associated releasable closure system(s) are configured and arranged such that such that a half of the releasable closure system (e.g. one half of a secondary zipper) extends along one long side edge of the gusset and a second complementary half of the releasable closure system (the other complementary half of a secondary zipper) extends along the other long side edge of the gusset. As can be appreciated from the exemplary embodiment shown in FIGS. 1 and 2 and the other exemplary embodiments described herein, gusset-associated releasable closure systems are desirable zippers, more desirably non-separating type zippers (also known as closed end zippers). For the sake of clarity, zipper(s) used as releasable closure system(s) in associated with gusset(s) are generally referred to herein as secondary zippers.

As can be appreciated from the exemplary embodiment depicted in FIGS. 1 and 2 and the other exemplary embodiments described herein, desirably the at least one expandable gusset extends substantially lengthwise between the upper and lower edges of the sleeve.

In the exemplary embodiment shown in FIGS. 1 and 2, the gusset (5) extends from the upper edge to the lower edge. In particular the gusset (5) is a strip of material, where one long side edge portion is attached to a sheet of material forming the main part (2) of the sleeve (1) and the other long side edge portion is attached to a second strip material (6) which is then connect to one of the complementary halves (3a) of the main zipper. To the exterior side of gusset, the outer, long edge portions of the two complementary halves of the secondary zipper (4) are attached either directly or indirectly to the long side edge portions of the gusset.

As can be appreciated from the exemplary embodiment shown in FIGS. 1 and 2 and the other exemplary embodiments described herein, when the gusset-associated releasable closure systems are zippers, in particular non-separating type zippers, desirably the zipper is arranged such that during the closing operation the zipper slider is pulled towards the upper edge, in other words towards the torso. Although for overall ease in use and construction, non-separating type zippers may generally be favorable, for embodiments including gussets which extend from the upper edge to the lower edge, separating-type zippers as secondary zippers may also be useful.

Figure 7:
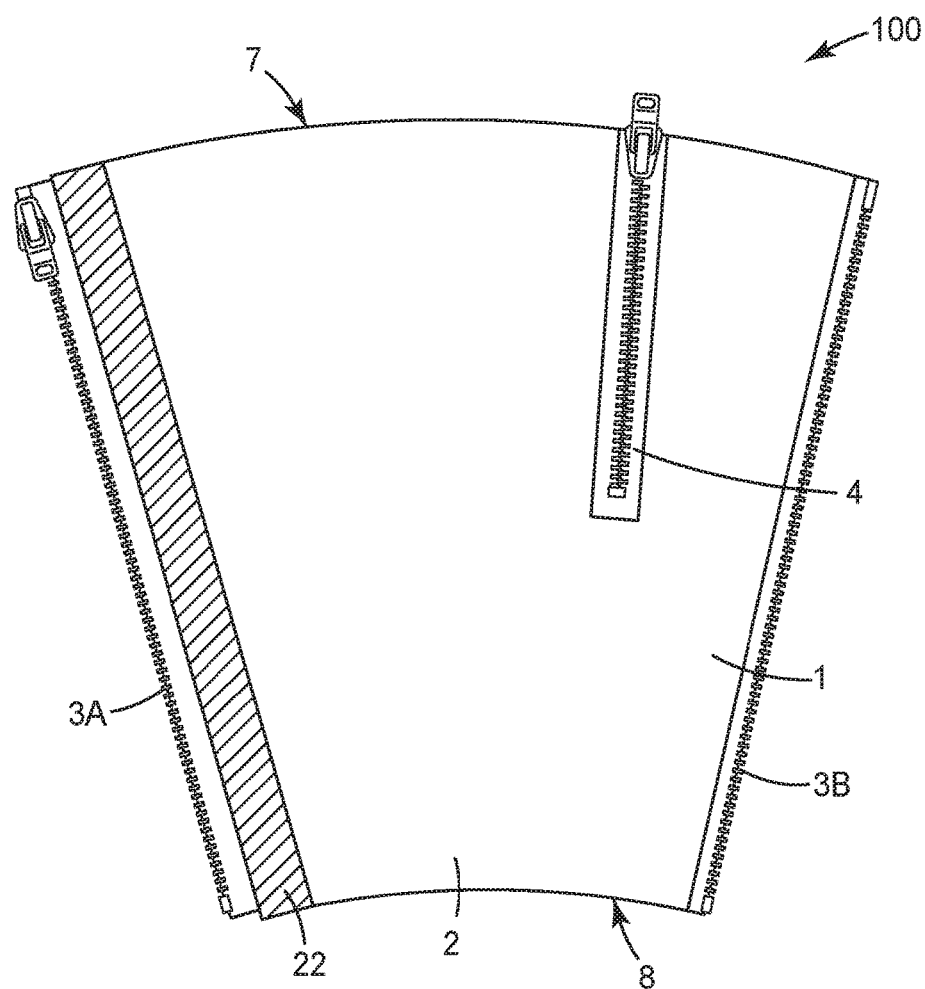
FIGS. 7 and 8 represent top views of two additional exemplary compression devices in accordance to the invention described herein.
Figure 8:
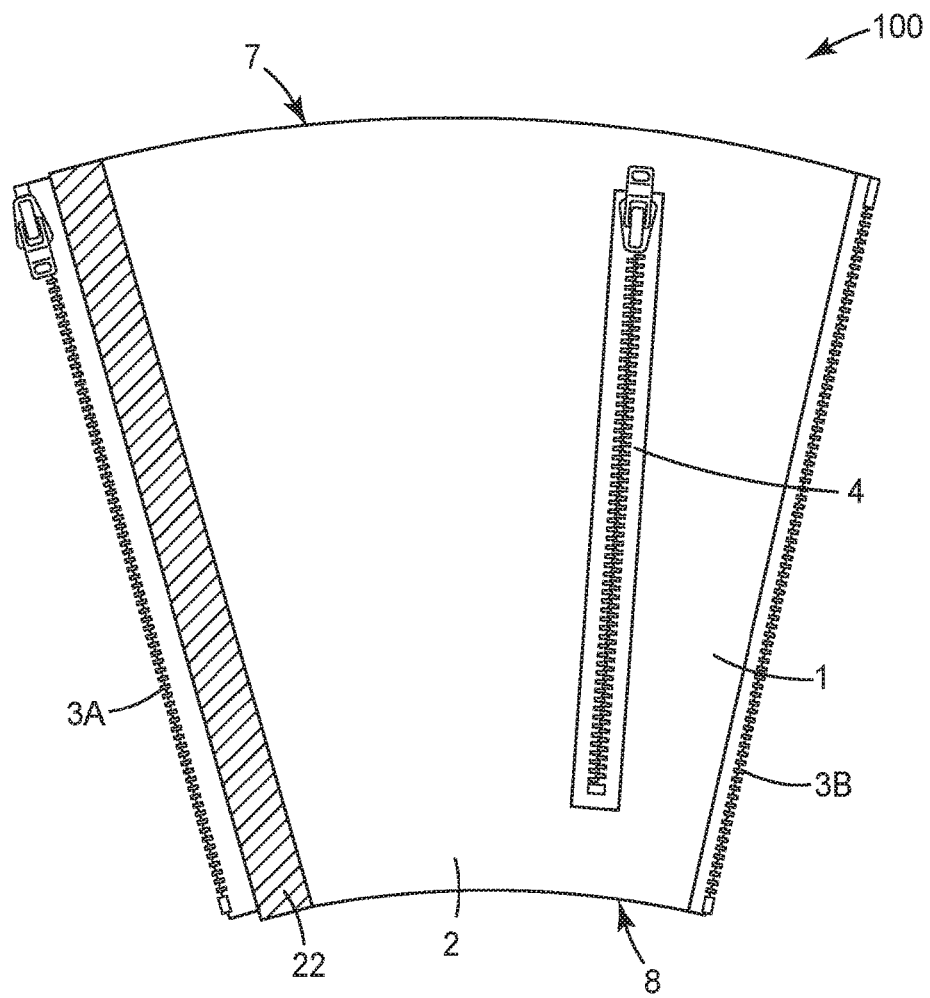

Gussets may extend a height that is less than the height of the sleeve from its upper to lower edge. Desirably gussets extend a height that is equal to or greater than 40% (more desirably a height that is equal to or greater than 50%, even more desirably a height that is equal to or greater than 60%, most desirably a height that is equal to or greater than 70%) of the height of the sleeve from its the upper to lower edge. For example, FIGS. 7 and 8 provides illustrations of two other exemplary embodiments of compression devices (100) in accordance to the invention described herein. Each of these exemplary embodiments has a gusset (5, not visible) with an associated secondary zipper (4) which extends a height that is greater than 40% of the height of the sleeve (1) from its the upper edge (7) to lower edge (8), but less than the height than the sleeve from the upper to lower edge.

Gussets may extend from the upper edge towards the lower edge (e.g. as shown in FIG. 7), or from the lower edge towards the upper edge, or they may extend from a point between the two edges towards one of the edges, but without reaching the two edges (e.g. as shown in FIG. 8). Gussets may be positioned near (e.g. adjacent) to the main zipper (e.g. as shown in FIG. 1) or distance thereto, in particular within the main part of the sleeve (e.g. as shown in FIGS. 7 and 8). Gussets may be substantially rectangular in shape (for example, as in from the exemplary embodiment depicted in FIGS. 1 and 2), or triangular in shape; diamond-shaped; canoe-shaped or rowboat-shaped.

As indicated above, the at least one gusset may be desirably made of a material having elasticity in at least the transverse direction of the sleeve. For example, in the exemplary embodiment depicted in FIGS. 1 and 2, the gusset (5) is made of a material having elasticity in as least the transverse direction of the sleeve, such that when the secondary zipper (4) is closed the gusset is in a relaxed state because the closed zipper prevents expansion (e.g. stretching) of the gusset, and when the secondary zipper is open, it is possible for the gusset to expand (e.g. by being stretched) between the two complementary halves of the secondary zipper so as to allow for an expansion of the width of the sleeve.

Desirably such gussets (i.e. gussets made of materials having elasticity in at least the transverse direction of the sleeve) are made of a material that exhibits in the transverse direction a tension equal to or greater than 0.02 N per mm width of material at 30% elongation, more desirably a tension equal to or greater than 0.05 N per mm width of material at 30% elongation. In addition or alternatively thereto, desirably such gussets are made of a material that exhibits at 10% elongation in the transverse direction a tension equal to or less than 0.5 N per mm width of material, preferably equal to or less than 0.3 N per mm width of material. Examples of such materials include elastic bands or elastic fabrics. e.g. elastic bands or fabrics including elastic fibers and/or yards (e.g. spandex or elastane fibers or yards made thereof). Examples of appropriate materials include tricot materials (for example available from Darlington Fabrics, Westerly, R.I., USA (e.g. Style No. 25530)) and elastic bands (for example available from TOKO-Kurzwaren, 69115 Heidelberg, Germany (e.g. "Gummiband" 300 mm wide, Article Nr. 001618)).

Figure 9:
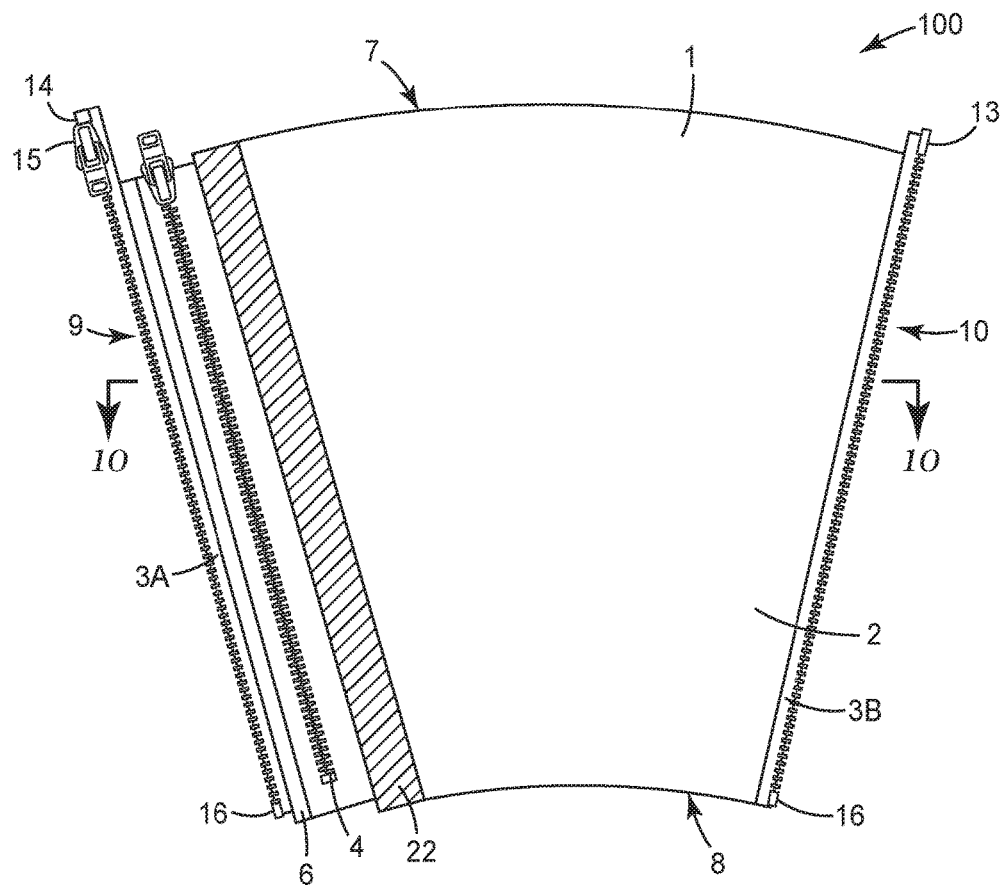
Figure 10:
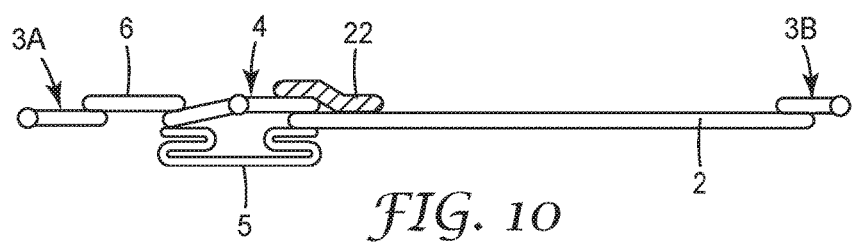
FIG. 10 shows a cross-sectional view of the exemplary embodiment shown in FIG. 9.

Alternatively, the at least one gusset may be made of a material that does not have elasticity in at least the transverse direction of the sleeve. Here desirably said gusset and its associated releasable closure system are configured and arranged such that when the releasable closure system is closed the gusset folds up behind the releasable closure system and when the releasable closure system is opened, said gusset can unfold between the opened parts of the releasable closure system. For example, FIGS. 9 and 10 depict a further exemplary embodiment which is identical to that shown in FIGS. 1 and 2, except that the gusset (5) is made of a material that does not have elasticity in at least the transverse direction. As can be appreciated from FIG. 10, when the secondary zipper (4) is closed the gusset is folds up behind the closed zipper and the closed zipper prevents the gusset from unfolding and thus expanding, and when the secondary zipper is open, it is possible for the gusset to expand by unfolding between the two complementary halves of the secondary zipper so as to allow for an expansion of the width of the sleeve.

Whether the gusset is made of a material having elasticity or not, favorably the sleeve is configured and arranged such that, in use, when the releasable closure system (e.g. secondary zipper) is opened, the gusset can expand (e.g. by stretching or unfolding) to a width up to and including 50 mm (more favorably up to and including 35 mm, most favorably up to and including 20 mm) in addition to that width that the gusset has when releasable closure system is closed.

As indicated above, sleeves of compression devices in accordance with the invention described herein may favorably includes two or more expandable gussets, each provided with a releasable closure system (e.g. a secondary zipper). It has been found that the use of multiple expandable gussets can further facilitate the lowering of the force needed to close the compression device about the body part (e.g. limb, torso, neck, head or neck/head combination) of the user.

Figure 11:
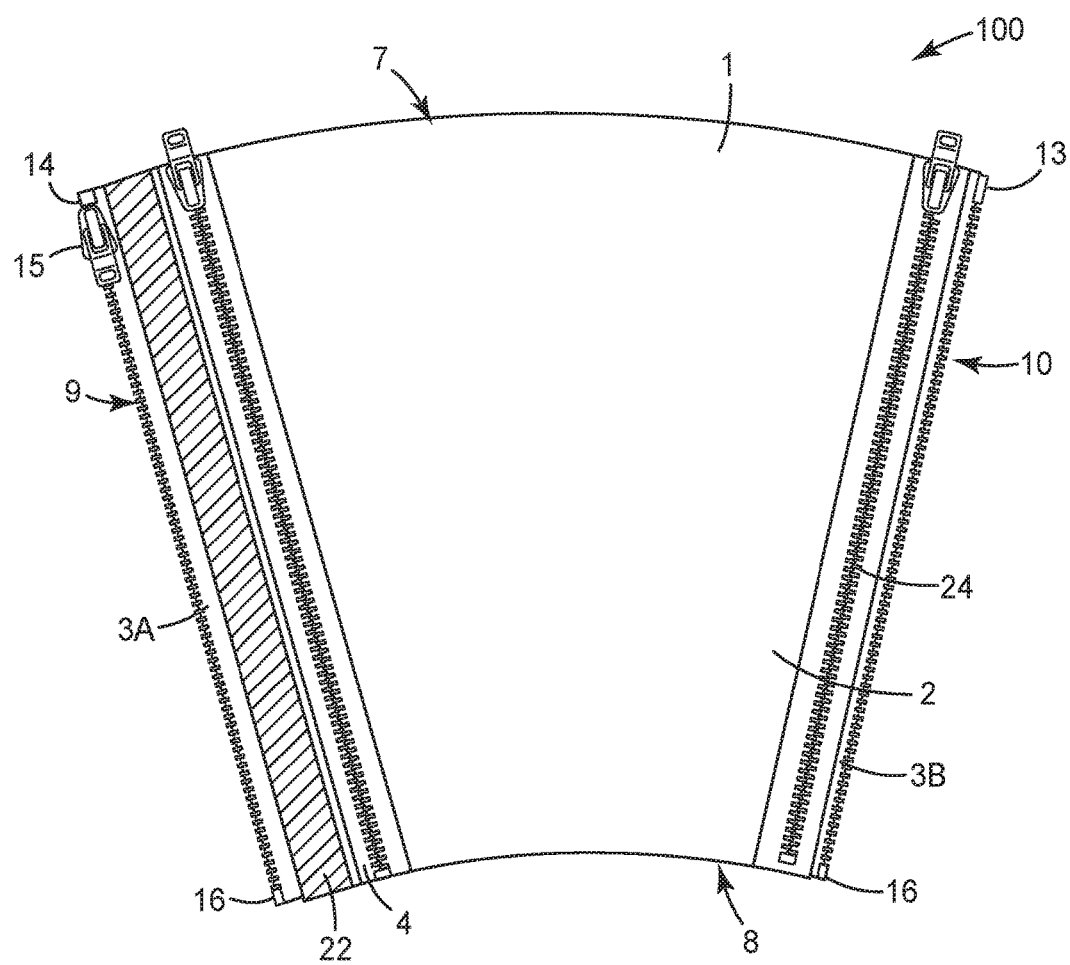
FIGS. 11 and 12 represent top views of yet two further exemplary embodiments of compression devices in accordance to the invention described herein.
Figure 12:
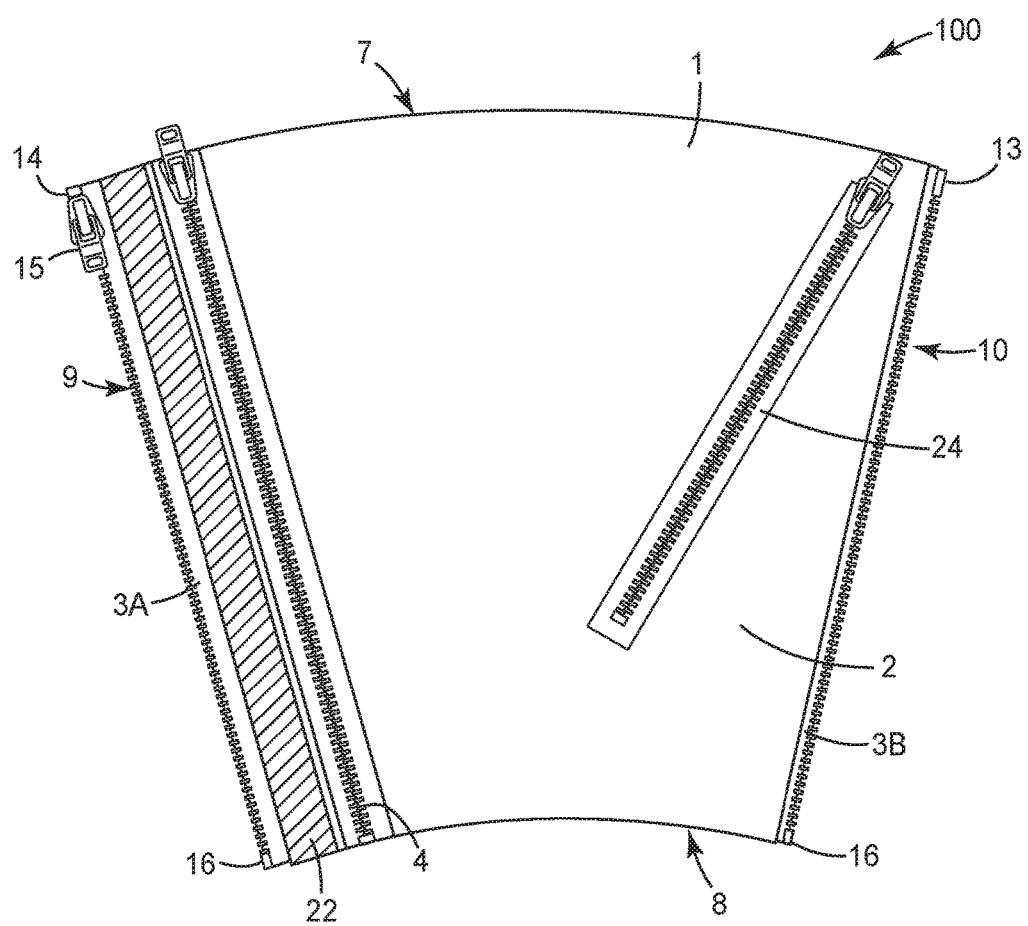

FIGS. 11 and 12 provide illustrations (top views) of two different exemplary embodiments each including two expandable gussets. These exemplary compression devices (100), similar to a number of the other exemplary embodiments, include a sleeve (1), an optional stiffener (22), a main zipper (3) as well as one expandable gusset (5, not visible) provided with a secondary zipper (4), this gusset extending essentially the complete height between the upper and lower edges (7,8) of the sleeve and positioned near one of the complementary halves (3A) of the main zipper (and thus distant to the second half (3B) of the main zipper). Both of these embodiments include a second expandable gusset (25, not visible) provided with its own releasable closure system (24), in particular a zipper, more particularly a non-separating zipper. In the exemplary embodiment shown in FIG. 11, the second gusset (25) with its secondary zipper (24) extends essentially the complete height between the upper and lower edges of the sleeve and is positioned near, in particular adjacent to, the second complementary half (3B) of the main zipper (and thus distant to first half (3A) of the main zipper). In the exemplary embodiment shown in FIG. 12, the second gusset (25) with its secondary zipper (24) is positioned within the main part (2) of the sleeve (1) extending substantially lengthwise between the upper and lower edges (7,8) of the sleeve (while not reaching either edge). Also as will be discussed further in conjunction with FIG. 13, the second gusset (25) with its secondary zipper (24) is disposed at an angle.

Figure 3A:
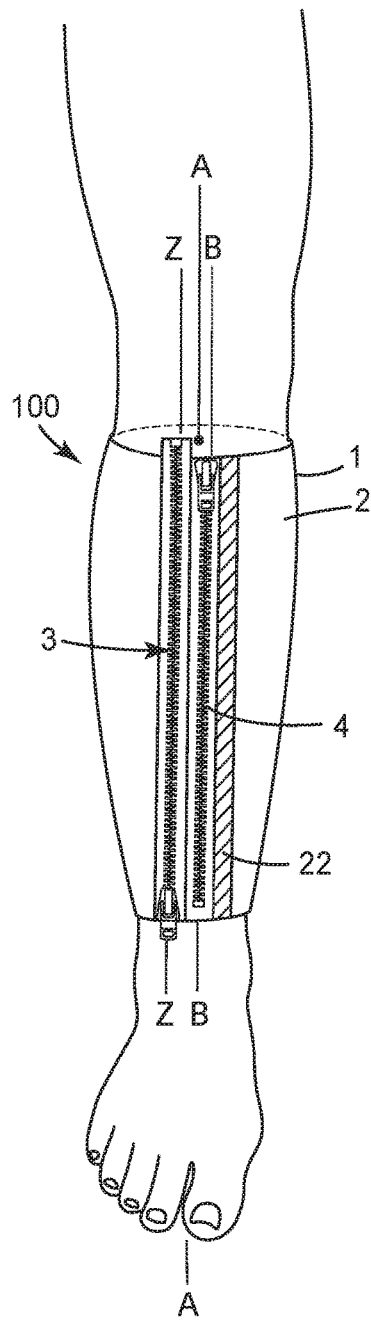
FIG. 3a represents a perspective view of the exemplary embodiment depicted in FIGS. 1 and 2 shown in use on the lower leg of a user.
Figure 3B:
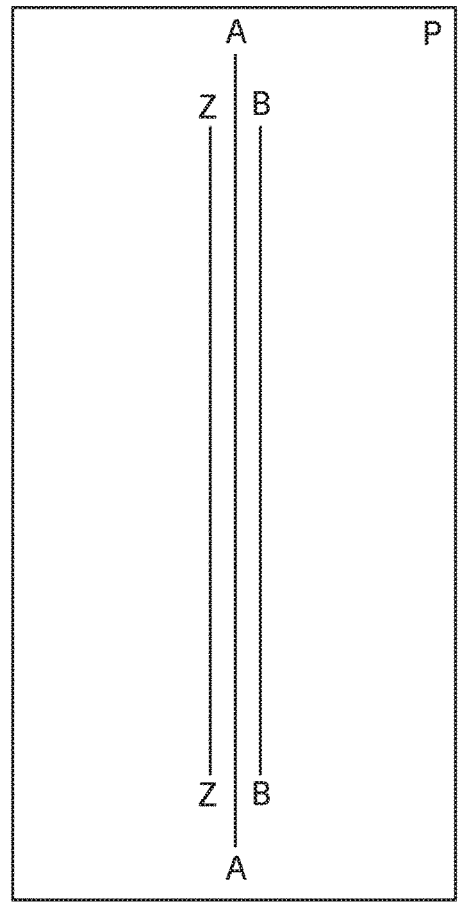
FIG. 3b shows a projection of the axes B and Z (which are depicted in FIG. 3a) onto a plane P containing the central axis A (that is also depicted in FIG. 3a).
Figure 13A:
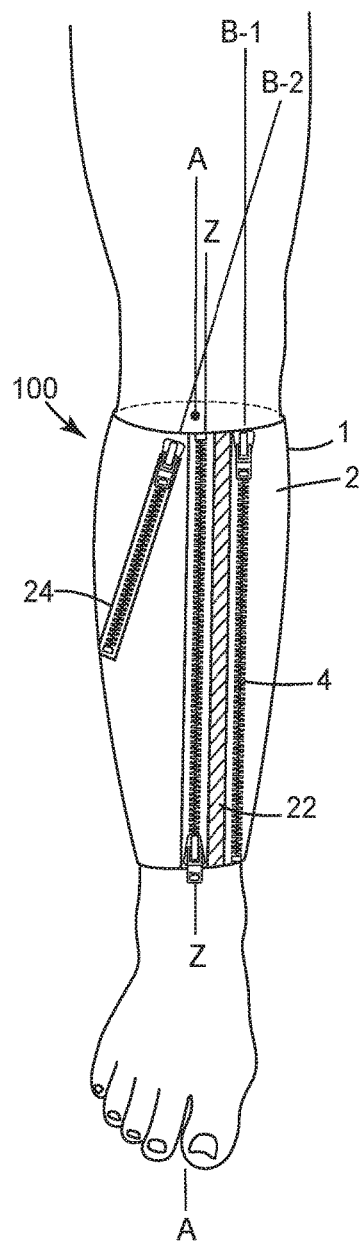
FIG. 13a represents a perspective view of the exemplary embodiment depicted in FIG. 12 shown in use on the lower leg of a user.
Figure 13B:
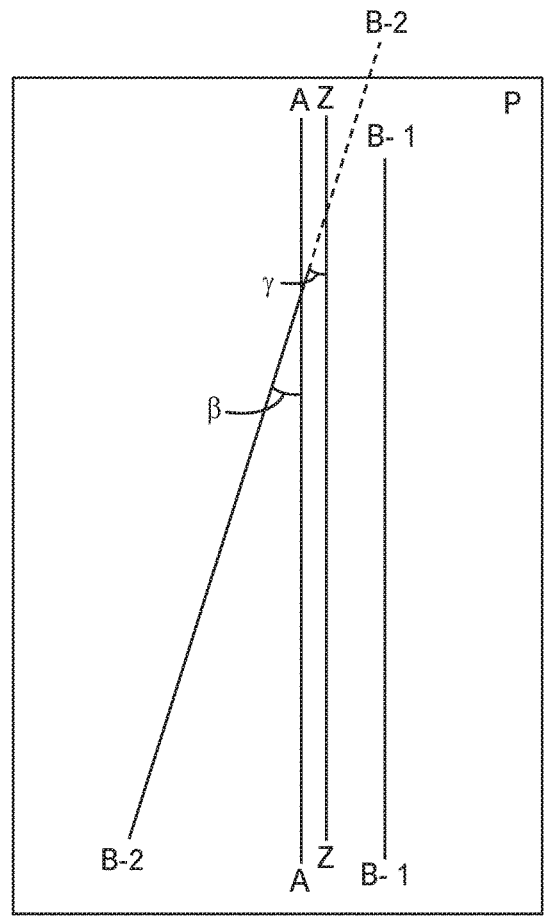
FIG. 13b shows a projection of the axes B-1, B-2 and Z (depicted in FIG. 13a) onto a plane P containing the central axis A (that is also depicted in FIG. 13a).

FIGS. 3a, 6a and 13a provide perspective views of the exemplary compression devices depicted in FIGS. 1 and 2, FIGS. 4 and 5, and FIG. 12, respectively, shown in use on the lower leg of a user. It can be appreciated from FIGS. 3a, 6a and 13a that once the compression device (100) is positioned onto the limb of the user, the sleeve (1) is disposed about a central axis (A). It can also be appreciated from these Figures that when the main zipper (3) as well as the gusset-associated releasable closure system(s) (4, and if applicable 24) are closed, the releasable closure system (in the exemplary embodiments the secondary zipper) extends along a second axis. In FIGS. 3 and 6 this axis is identified as "B", and in FIG. 13, since there are two secondary zippers (4, 24), the relevant axes are identified "B-1" and "B-2", respectively. Referring to FIGS. 3b, 6b and 13b, which show the projection of these axes onto a plane (P) containing the central axis (A), it can be seen that each of the secondary zippers (4) in the exemplary embodiments depicted in FIGS. 1 and 2 and in FIGS. 4 and 5, as well as the first secondary zipper (4) in the exemplary embodiment depicted in FIG. 12 extend along an axis (B or B-1) that, relative to the projection of said axis onto said plane (P), is in parallel alignment or essentially parallel alignment with the central axis (A). Referring to FIG. 13b, it can be recognized that second secondary zipper (24) in the exemplary embodiment depicted in FIG. 12 extends along an axis (B-2) that, relative to the projection of said axis onto said plane (P), is inclined forming an acute angle (β) of 18° relative to the central axis.

For embodiments where the sleeve will be disposed about a central axis (A), said central axis lying in a plane (P), when the compression device is in use on the respective body part of the user, it has been found favorable to configure the compression device such that when the compression device is in use on the body part (e.g. a limb, torso or neck) of the user and when the main zipper and releasable closure system (e.g. secondary zipper) are closed, the releasable closure system extends along a second axis (B), wherein relative to a projection of said second axis (B) onto said plane (P) containing the central axis (A), the second axis is either in parallel alignment or inclined forming an acute angle (β) up to 45° inclusive relative to the central axis. In more favorable embodiments of the latter, said acute angle (β) may be equal to or less than 35°, even more favorably equal to or less than 30°, yet even more favorably equal to or less than 25°, most favorably equal to or less than 20°. It is to be appreciated that when the compression device is in use on the body part (e.g. limb, torso or neck) of the user, it is possible that the closed releasable closure system, i.e. the closed secondary zipper, may not extend along a perfectly straight axis, i.e. its projection may be curved due to tension and particular body part (e.g. leg, torso, neck) geometry of the user, and in such cases the relevant axis along which the releasable closure system extends may be defined as being the axis resulting from a best linear fit (linear regression) to the projected curve.

Returning to FIGS. 3a, 6a and 13a, it can be seen that when the compression device (100) is positioned onto the body part, here in particular the limb, of the user and the main zipper (3) as well as the gusset-associated releasable closure system(s) (4, 24) are closed, the main zipper extends along a third axis (Z). Referring to FIGS. 3b, 6b and 13b which shown the projection of this third axis (Z) onto a plane (P) containing the central axis (A), it can be seen that each of the main zipper in the exemplary embodiments depicted in FIGS. 1 and 2 and in FIG. 12 extend along an axis (Z) that, relative to the projection of said axis onto said plane (P), is in parallel alignment or essentially parallel alignment with the central axis (A), while the main zipper in the exemplary embodiment depicted in FIGS. 4 and 5 extends along an axis (Z) that, relative to the projection of said axis onto said plane (P), is inclined forming an acute angle (α) of 12° relative to the central axis (A).

For embodiments where the sleeve will be disposed about a central axis (A), said central axis lying in a plane (P), when the compression device is in use on the respective body part of the user, it has been found favorable to configure the compression device such that when the compression device is in use on the body part (e.g. limb, torso or neck) of the user and when the main zipper and releasable closure system(s) (e.g. secondary zipper (s)) are closed, the main zipper extends along a third axis (Z), wherein relative to a projection of said third axis (Z) onto said plane (P) containing the central axis (A), the second axis is either in parallel alignment or inclined forming an acute angle (α) up to 45° inclusive relative to the central axis. In more favorable embodiments of the latter, said acute angle (α) may be equal to or less than 35°, even more favorably equal to or less than 30°, yet even more favorably equal to or less than 25°, most favorably equal to or less than 20°. It is to be appreciated that when the compression device is in use on the body part (e.g. limb, torso or neck) of the user, it is possible that the closed main zipper may not extend along a perfectly straight axis, i.e. its projection may be curved due to tension and particular body (e.g. leg, torso or neck) geometry of the user, and in such cases the relevant axis along which the main zipper extends may be defined as being the axis resulting from an best linear fit (linear regression) to the projected curve.

For embodiments where the sleeve will be disposed about a central axis (A), said central axis lying in a plane (P), when the compression device is in use on the respective body part of the user, favorably the compression devices are configured such that when the compression device is in use on the body part (e.g. limb, torso, neck) of the user and when the main zipper and releasable closure system(s) (e.g. secondary zipper (s)) are closed, the second axis (B) and third axis (Z) are either parallel to one another or inclined to one another such that the angle (γ) formed at a theoretical point of intersection between the second and third axes is equal to or less than 30°. This is best illustration by again referring to FIGS. 3b, 6b and 13b which shown the projection of such axes onto a plane (P) containing the central axis (A). It can be seen in FIG. 3b that for the exemplary embodiment depicted in FIGS. 1 and 2, the axis along which the secondary zipper (4) extends, i.e. the second axis (B), and the axis along which the main zipper (3) extends, i.e. the third axis (Z) are, relative to the projections of these axes onto the plane (P), parallel or essentially parallel to one another. The same holds true for the exemplary embodiment depicted in FIG. 12 having regard to the main zipper (3) and first secondary zipper (4). However for this exemplary embodiment, it can be in FIG. 13b that the axis along which the second secondary zipper (24) extends, i.e. the second axis (B-2), and the axis along which the main zipper (3) extends, i.e. the third axis (Z) are, relative to the projections of these axes onto the plane (P), inclined to one another such that the angle (γ) formed at a theoretical point of intersection between the these axes is 18°. The exemplary embodiment depicted in FIGS. 4 and 5 is similar in this regard. Moreover it can be seen in FIG. 6b that in this exemplary embodiment, the axis along which the secondary zipper (4) extends, i.e. the second axis (B), and the axis along which the main zipper (3) extends, i.e. the third axis (Z) are, relative to the projections of these axes onto the plane (P), inclined to one another such that the angle (γ) formed at a theoretical point of intersection between the these axes is 12°.

As mentioned above, compression devices described herein may also be configured and arranged, such that when the compression device is in use on the respective part of the user, the sleeve may not be disposed about a central axis (A). In particular this may hold true for compression devices configured and arranged for use on a portion of a head of the user or a portion of the neck and head in combination. As indicated above such devices may be configured for example like a fitted hood covering the neck, chin and over the head leaving the face free where the zipper and the releasable closure system may be provided either along the top and back of the head or along the front down the chin/jaw and front of the neck. For such embodiments, desirably the axes along which the zipper and the releasable closure system run are desirably parallel to one another or substantially parallel to one another (i.e. inclined to one another such that the angle formed at a theoretical point of intersection between the axes is equal to or less than 5°).

Figure 14A:
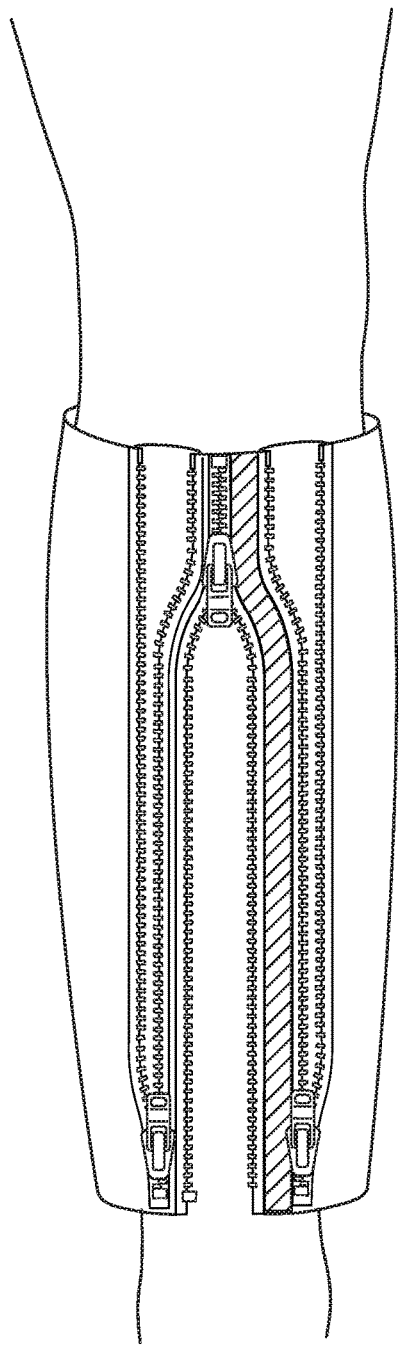
FIG. 14 a to d provide a series of illustrations showing perspective views of the exemplary compression device depicted in FIG. 11 during its application onto the limb on a user.
Figure 14B:
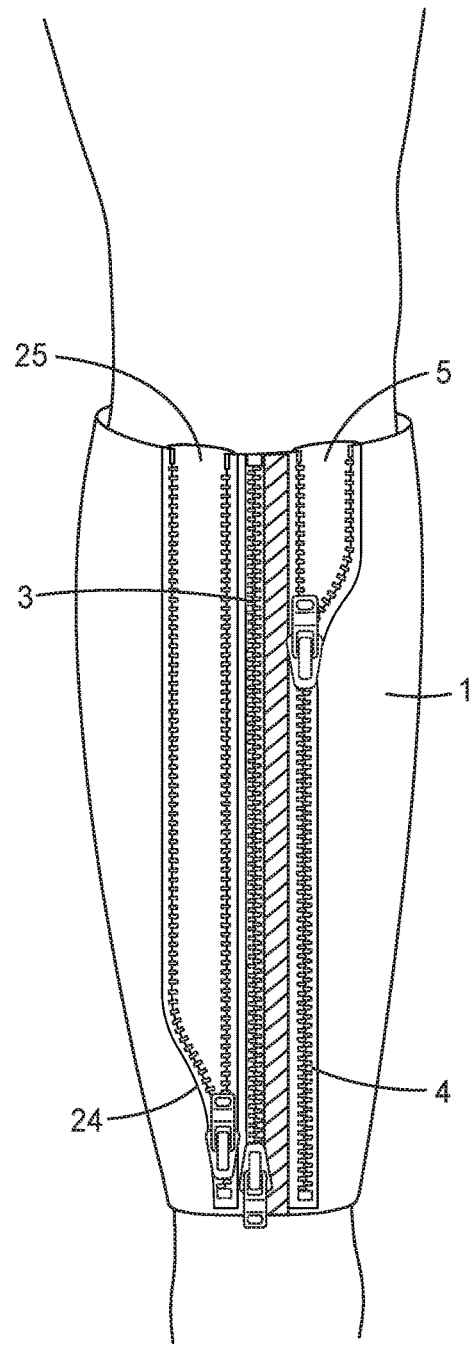

FIG. 14 provides a series of illustrations (a to d) showing various perspective views of the exemplary embodiment depicted in FIG. 11 during its application onto the body part, in particular the limb (more particularly here the lower leg) of the user. For ease in viewing, reference numbers are only shown in FIGS. 14b and 14d. Initially the main zipper (3) and both the secondary zippers (4, 24) are opened, i.e. unzipped. As shown in FIG. 14a, the compression device (100), in particular the sleeve (1) thereof, is generally positioned about the body part, here the limb, of the user, and once generally placed into position, the insert pin of one half of the main zipper is inserted into the box on the other half of the main zipper (3), and the main zipper is zipped together. As can be appreciated from FIG. 14b, once the main zipper is completely closed, one can then close the secondary zippers. The two secondary zippers may be closed simultaneously or sequentially. The illustrations here show the latter option. In FIG. 14b, the first secondary zipper (4) is partly closed. Once this first secondary zipper is completely closed, then the second secondary zipper (24) is closed. In FIG. 14c the first secondary zipper (4) is completely closed and the second secondary zipper (24) is partly closed. It will be appreciated from FIGS. 14a to c that when the main zipper is closed or partially closed and the secondary zippers are still open or only partially closed, the two gussets (5, 25) can expand between the complementary halves of their associated secondary zippers (4, 24). Moreover each gusset is stretched due to the tension placed on the compression device once the main zipper was closed (or even partly closed). As shown in FIG. 14d, once the both secondary zippers are completely closed, the compression device is fully applied onto the lower leg of the user.

Compression devices, in particular the sleeves thereof, can be provided in different sizes to accommodate the difference in the size of body parts (e.g. limbs versus torsos or necks or heads; or e.g. relative to just limbs arms versus legs) as well as the general difference in sizes of a particular body part (e.g. limb). Compression devices suitable for use with necks and heads will often be used for both, i.e. configured to cover a portion of both the neck and head of the user.

Compression devices described herein are particularly suitable for use on limbs, in particular the lower leg including the calf (e.g. for treating among other things venous leg ulcers and lymphoedema of the leg). In regard to the latter, for example considering the size of an adult human lower leg, including those persons suffering from lymphodemia, can range from around 130 to 420 mm in circumference at the ankle and around from 280 to 650 mm in circumference at their widest point, it could be possible to provide compression devices in for example seven standard (width) sizes, e.g. XS, S; M, L, XL, XXL, XXXL, aimed to cover 80% of the potential relevant circumferential sizes of the potential users while the remaining 20% could be provided for by special order. In addition, considering the length of an adult human lower leg can range from around 20 cm to 40 cm, it could be possible to provide in conjunction with the standard (width) sizes mentioned above, three height sizes, e.g. short, average and, tall, again aimed to cover 80% of the potential relevant lengths of the potential users. In regard to the standard width sizes, the number of standard sizes to cover 80% the potential relevant circumferential sizes of the potential users could be reduced by for example providing compression devices configured such that the width of the sleeve could be readily adjusted by the user or the care-giver applying the compression device onto the limb of the user. In the following three exemplary embodiments of such width-adjustable compression devices will be discussed.

FIGS. 15 and 16 provide illustrations of a top view and cross-sectional view of an exemplary compression device (100) that can be adjusted in its width. Similar to other embodiments described herein, this exemplary embodiment includes a sleeve (1) having an upper edge (7), a lower edge (8), two sides edges (9, 10), wherein the first side edge (9) is provided with one half (3A) of a separating zipper and the second side edge (10) is provided with a complementary half (3B) of the separating zipper and an expandable gusset (5) provided with a releasable closure system (4), in particular a secondary zipper, more particular a non-separating zipper, extending along the length of said gusset as well as an optional stiffener (22). In addition, the sleeve favorably comprises a main part (2) for substantially covering a main portion of the body part (e.g. limb, torso, neck, head or neck/head combination), said main part extending from the second side edge (10) towards to the first side edge (9), and wherein the exterior surface of the main part is provided with two or more (e.g. three) separating zipper halves (23B, 33B, 43B) positioned in series along the transverse (and thus circumferential) direction (C), each said zipper half extending from the upper edge and to lower edge of the sleeve and being complementary to the half (3A) of the separating zipper provided on the first side edge, Adjustment in size can be appropriately carried out by mating the half (3A) of the separating zipper provided on the first side edge (9) with one of the provided series of complementary halves (3B, 23B, 33B, 43B). In the particular exemplary embodiment illustrated, four different widths are possible.

Figure 17:
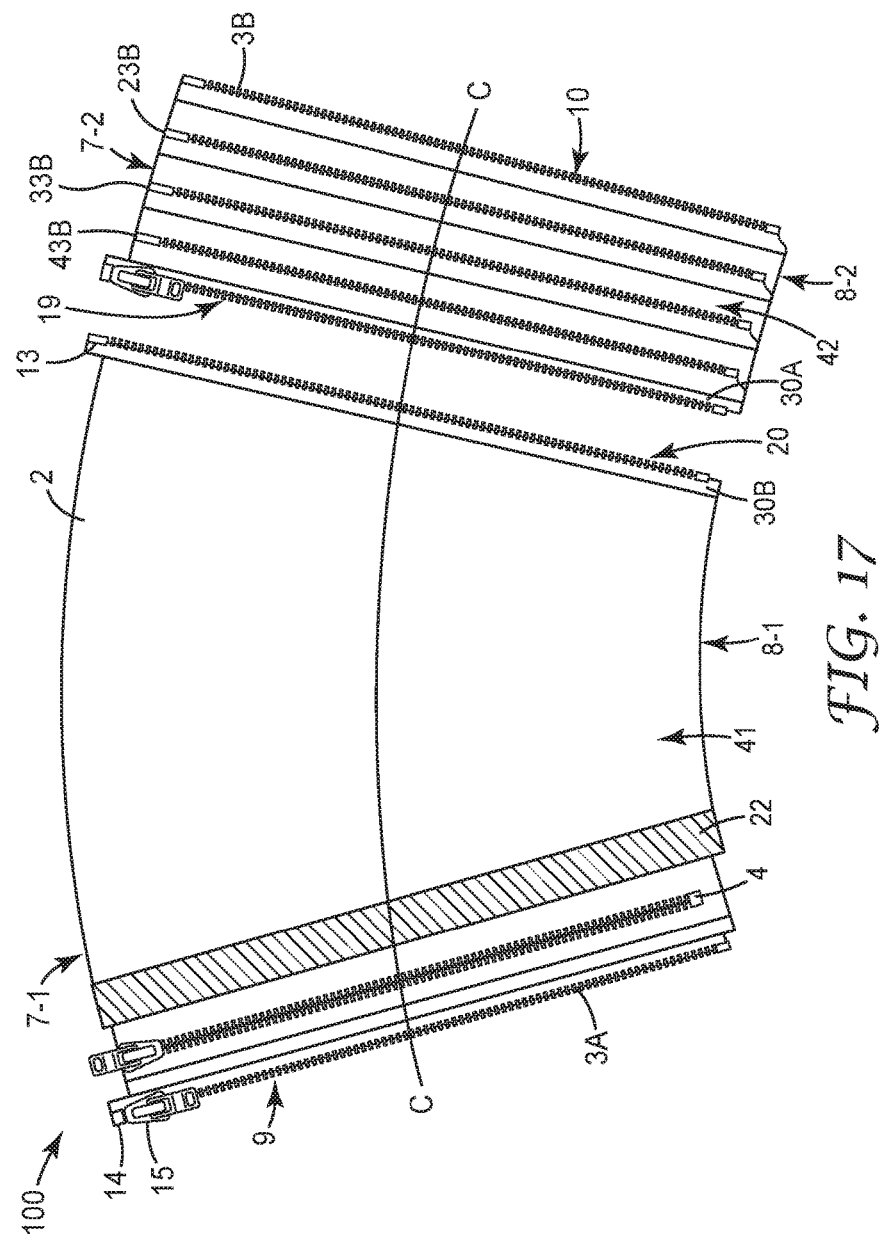
FIG. 17 represents a top view of another exemplary width-adjustable compression device in accordance to the invention described herein.

FIG. 17 provides an illustration of a top view and cross-sectional view of another exemplary compression device (100) that can be adjusted in its width. This exemplary embodiment differ from the other exemplary embodiments described herein, in that the sleeve (1) comprises two sub-components, the first sub-component (41) including the first half (3A) of the main zipper, that is favorably a separating zipper, and the second sub-component (42) including the second half (3B) of the main zipper, wherein in use the two sub-components are positioned in series (in particular adjacent to one another) along the transverse (and thus circumferential) direction (C) and releasably attached to one another. FIG. 17 shows the two sub-components (41, 42) detached from one another. As can be appreciated from FIG. 17, each of the sub-components generally has an upper edge (7-1, 7-2) and a lower edge (8-1, 8-2) and when the sub-components are releasably attached to one another thus edges then provide the overall upper and lower edges of the sleeve. The first sub-component (41) includes the first side edge (9) with the first half (3A) of the main zipper and a lateral side (20) opposite the first side edge. The second sub-component (42) includes the second side edge (10) with the second half (3B) of the main zipper and a lateral side (19) opposite the second side edge. It will be appreciated that when the two sub-components are attached to each other, ready for use, the aforesaid mentioned lateral edges will located towards the interior of the sleeve. The first and second sub-components of the sleeve are releasably attached to one another, for example, via the usage of a releasable closure system (tertiary releasable closure system), so that the lateral edge (20) of one sub-component (41) is positioned towards the lateral edge (19) of the other sub-component (42). Favorably the releasable closure system is configured and arranged such that a half of the releasable closure system (30B) extends along the lateral edge (20) of the first sub-component (41) and a complementary half of the releasable closure system (30A) extends along the lateral edge (19) of the second sub-component (42). As can be seen in FIG. 17, the releasable closure system may be a separating zipper. For the sake of clarity, this zipper is referred to herein as the tertiary zipper. Favorably the first sub-component (41) comprises a main part (2) for substantially covering a main portion of the body part (e.g. limb, torso, neck, head or neck/head combination), in particular extending from the lateral edge (20) of the first sub-component towards to the side edge (9) with the half (3A) of the main zipper. It will be appreciated that the first sub-component (41) is configured the same as the exemplary embodiment depicted in FIGS. 1 and 2, and reference is made to the description of this embodiment. Favorably, the exterior surface of the second sub-component (42) is provided with two or more (e.g. three) separating zipper halves (23B, 33B, 43B) positioned in series along the transverse (and thus circumferential) direction (C), each said zipper half extending from the upper edge (7-2) and to lower edge (8-2) of the second sub-component and being complementary to the half (3A) of the separating main zipper on the first sub-component. Adjustment in size can be appropriately carried out by for example mating the half (3A) of the separating zipper provided on the first sub-component (41) with one of the provided series of complementary halves (3B, 23B, 33B, 43B) on the second sub-component (42), or alternatively simply mating the two complementary halves on the first sub-component without even using the second sub-component. Moreover, five different widths are possible: a most narrow width based on just the shown first sub-component (which in fact is equivalent to the exemplary embodiment depicted in FIGS. 1 and 2) and four progressively larger widths resulting from appropriately attaching the two sub-components together where the second sub-component can be described as an extension to the first sub-component. In the exemplary embodiment illustrated in FIG. 17, an expandable gusset (5) with its associated releasable closure system, e.g. the secondary zipper (4) is included in the first sub-component (41). The gusset with its releasable closure system could alternatively be included in the second sub-component, for example between the half (30A) of the tertiary zipper located on lateral side of the second sub-component and the zipper half (43B) in the series of complementary halves which is located near the tertiary zipper-half. For such alternative embodiments, the second sub-component would always need to be used to be sure that the sleeve comprising the first and second sub-component comprises at least one expandable gusset. In the event, such a two sub-component sleeve would include a multiple number of expandable gussets, they could be provided either in first sub-component or in the second sub-component or in both.

FIGS. 18 to 21 provide illustration of a third exemplary compression device (100) that can be adjusted in its width, in particular via overlapping and/or trimming. Similar to the exemplary embodiment depicted in FIG. 17, the sleeve (1) of this exemplary embodiment comprises two sub-components: a first sub-component (41) including the first half (3A) of the main zipper and the second sub-component (42) including the second half (3B) of the main zipper, which is favorably a separating zipper, wherein the two sub-components are releasably attached to one another and positioned in series along the transverse direction (C) of the sleeve (see e.g. FIGS. 20 and 21). In this exemplary embodiment, the first sub-component (41) includes a main part (2) of the sleeve for substantially covering a main portion of the body part (e.g. limb, torso, neck, head or neck/head combination). In addition the first sub-component (41) comprises an expandable gusset (5) with an associated secondary zipper (4) as well as an optional stiffener (22). Referring to FIGS. 18 and 19, it can be recognized that in use the two sub-components are positioned in series (in particular overlapping one another) along the transverse (and thus circumferential) direction (C) and releasably attached to one another. As can be easily recognized in FIGS. 20 and 21, each of the sub-components (41, 42) has a lateral edge (20,19) opposite the side edge (9,10) with the respective halves (3A, 3B) of the main zipper. It will be appreciated that the lateral edge may straight or alternatively irregular in form, for example the lateral edge (19) of the second sub-component (42) is castellated in form. In this exemplary embodiment, the first and second sub-components of the sleeve are favorably, releasably attached to one another using a mechanical fastening closure system. In particular, the interior surface of at least the portion of the second sub-component (42) that is near or adjacent to lateral edge of the second sub-component is provided with hook, stem and/or cup-shaped fasteners and the exterior surface of at least the portion of the first sub-component that is near or adjacent to lateral edge of first sub-component has a structure or is provided with a structure that is adapted to be engaged by said fasteners. (The respective lateral edge portions of the first and second sub-components are labeled with reference numbers 23 and 24, respectively, in FIGS. 20 and 21.) In regard to the latter, examples of materials that may be adapted to be engaged by hook, stem and/or cup-shaped fasteners include fluffy non-woven materials, extrusion-bonded loop materials, knitted loop materials and/or hooks Adjustment in size can be appropriately carried out by for example placing the fastener-equipped, interior portion of the second sub-component onto the fastener-engageable, exterior portion of the first sub-component, such that these portions, in particular the lateral edge portions (23,24), of the two releasably attached sub-components overlap completely or in part so that the desired circumference of the sleeve is achieved. It will be appreciated that the width of the sleeve is essentially freely adjustable (within a maximum and minimum width range given by the overall configuration and dimensions of the particular compression device) depending on the particular position at which the second sub-component is releasably attached onto the first sub-component (or vice versa). As illustrated in FIGS. 18 and 19, the second sub-component (42) may be releasably attached onto the first sub-component (41) such that the second side edge (10) with its half (3B) of the main zipper of second sub-component is positioned adjacent to the exterior surface of the first sub-component, in particular the main part (2) thereof, so that the lateral edge (20) of the first sub-component extends beyond the second side edge (10) of the second sub-component (42). This may happen when narrow sleeve widths are desired. It may be desirable to configure and arrange first sub-component such that the lateral edge portion of the first sub-component is trimmable, so that in those instances where the adjusted width is so narrow that the first sub-component extends beyond the main-zipper-half-equipped side edge of the second sub-component, the over-extending lateral edge portion of first sub-component could be then trimmed away. Alternatively, the over-extending lateral edge portion could be left as is, and when the sleeve is in use this portion would located towards the interior as a sort of partial under-winding. In the exemplary embodiment illustrated in FIGS. 18 to 21, one expandable gusset (5) with its associated releasable closure system, e.g. the secondary zipper (4) is included in the first sub-component (41). The gusset with its releasable closure system could alternatively be included in the second sub-component, for example adjacent to the half of the main zipper. In the event, such a two sub-component sleeve would include a plurality of expandable gussets, they could be provided either in first sub-component or in the second sub-component or in both.

In methods of applying compression devices comprising a sleeve including first and second sub-components as described herein, such methods would generally comprise attaching (i.e. releasably attaching) the first and second sub-components together prior to step a) in the method outlined above. In particular in order to adjust the size to a needed and/or desired width, one may carry out the following: (i) close the main zipper, open the at least one expandable gusset by opening its releasable closure system and detach the first and second sub-components of the sleeve (the closing. opening and detaching may be done in any order); (ii) position the sleeve about the respective body part (e.g. limb, torso, neck, head or neck/head combination) of the user, and (iii) (releasably) attach the first and second sub-component such that the needed and/or desired width is achieved. When positioning the sleeve about the respective body part (e.g. limb, torso, neck, head or neck/head combination) of the user, the user or care-giver applying the compression device can visually assess what is the needed and/or desired width, and the attachment of the first and second sub-component to give the appropriate width can be then performed either while the sleeve is still in position about the body part (e.g. limb, torso, neck, head or neck/head combination) or separately from the body part (e.g. limb, torso, neck, head or neck/head combination), as appropriate. Once the first and second sub-components are attached, the compression device can then be applied for example as described above. If during compression therapy, there is a significant change in the width of the body part (e.g. limb, torso, neck, head or neck/head combination), for example a reduction in width as a result of effective compression therapy, it may be necessary and/or desirous to re-adjust the width. It will be recognized that in step (i) listed above, instead of opening the at least one expandable gusset, one could alternatively close the at least one expandable gusset by closing its releasable closure system.

For compression devices including two or more expandable gussets as described herein, adjustment of width could also be achieved via the second (and if applicable third and so on) gusset. Moreover, in use of such a compression device, at the beginning of compression therapy only one of the two or more expandable gussets would be closed, and subsequently once the reduction of body part (e.g. limb, torso, neck, head or neck/head combination) volume and width is great enough as a result of effective compression therapy, the other gusset(s) may then be closed.

Experimental

Test Methodology for Tensio and Recovered Elongation

Tension and recovered elongation were determined through measurements based on BS EN 14704-1:2005 "Determination of the elasticity of fabrics,—Part 1: Strip tests": Method A, Knitted Fabrics (see inter alia sections 8.2.2 & 9.2.1) with the following variations and/or conditions to given method: (i) strip test specimens were cut with their length parallel to transverse (circumferential) direction and specimen size was 100 mm in length and 25 mm wide (see 8.2.2.1.1); (ii) gauge length was set at 70 mm (see 9.2.1.1); (iii) extension rate was set at 500 mm/min (as given in section 9.2.1.2); (iv) required cycling limits were set to said gauge length and a fixed elongation of 30% (see subsection 9.2.1.3); (v) during cycling and elongation up to fixed elongation of 30%, the force measured at 10% elongation was recorded in addition to force measured at 30% elongation; (vi) on final cycle testing machine was held at maximum elongation (i.e. 30% elongation) for 1 minute (see NOTE 2 of 9.3); and (vii) recovery period was 30 min (see NOTE 3 of 9.3); (viii) test specimens were preconditioned for 24 hours at 50% RH and 20° C.; (ix) number of test specimens were three; and with the following results: (a) tension at 30% elongation is the recorded maximum force at 30% elongation from the final cycle divided by the width size (i.e. 25 mm) of the specimen; (b) tension at 10% elongation is the force recorded at 10% elongation during the final cycle divided by the width size (i.e. 25 mm) of the specimen; and (c) percent recovered elongation is (100—un-recovered elongation in percentage) and percent un-recovered elongation is $[(Q-P)/P]\times 100$ where Q is the distance between applied reference marks (mm) after specified hold and recovery periods and P is the initial distance between reference marks (mm).

EXAMPLES

In the following a compression sleeve made of a flexible material having elasticity in its transverse (circumferential)

direction and being suitable for compression therapy on the lower leg of an adult was used. The sleeve included one main, separable zipper for opening and closing the sleeve, and when the main zipper was opened, the sleeve had substantially a trapezoidal shape with slightly curved upper edge and lower edges (upper edge convex and lower edge concave) and two lateral side edges, each of the lateral edges provided with one of the complementary halves of the main, separable zipper. The angles between the upper edge (essentially the long transverse side of the trapezoid) and each of the lateral sides were approximately 90° and 90°, while the angles between the lower edge (essentially the short transverse side of the trapezoid) and each of the lateral sides were approximately 90° and 90°. It is to be appreciated that despite the fact that the sleeve is generally trapezoid in shape the angles are 90° due to the fact that the upper and lower transverse edges are curved. If the curved upper and lower edges would be replaced with non-curved (straight) edges, the angles between the upper edge and each of the lateral sides would be approximately 75 and 75° and the angles between the lower edge and each of the lateral sides would be approximately 105° and 105°. The sleeve included as inserts two rectangular band-shaped gussets extending from the lower edge to the upper edge of the sleeve. Each gusset included a non-separable zipper extending along its length, i.e. one complementary half of the zipper extended along one long side of the gusset and provided on the exterior surface of the sleeve and the other complementary half along the other long side of the gusset again on the exterior surface of the sleeve, with the closed, non-separable end of the zipper being located adjacent to the upper edge of the sleeve. In a non-stretched state the width of gusset is essentially the width of the closed secondary zipper, i.e. 25 mm, the width between the longitudinal seams of the two complementary halves of the secondary zipper. In the closed position of the zippers, the secondary zippers ran parallel to the main zipper and were spaced 2 cm apart from the main zipper. In use on the limb of the user, the sleeve is disposed about a central axis lying in a plane, and when the main zipper and secondary zippers were closed, relative to a projection of the axis along which the main zipper extended onto the plane containing the central axis, the axis along which the main zipper extended was in parallel alignment relative to the central axis. Similarly In use on the limb of the user, when the main and secondary zippers were closed, relative to a projection of each of the axes along which each of secondary zippers extend onto the plane containing the central axis, each said axis was in substantially parallel alignment with the central axis. The gusset inserts were made of an expandable a tricot material obtained from Darlington Fabrics (Style No. 25530; 322 g/m² (9.5 oz/yd²); 1.016 mm (0.04 in) thick; 92% nylon and 8% spandex fiber content) having elasticity in the transverse (circumferential) direction and exhibiting in said direction a measured tension of 0.09N per mm (7% standard deviation) width at 30% elongation (, recovered elongation of 97% (4% standard deviation) as well as a measured tension of 0.015N per mm width at 10% elongation (12% standard deviation). The sleeve with all three zippers open had in a non-stretched state a height of 36 cm from its upper edge to lower edge, and a width of 26 cm along its lower edge, a width of 40 cm along its upper edge and a width of approximately 37 cm at 10 cm from the upper edge. The sleeve is referred to as the "Test Sleeve 3 Zippers".

In another example a test sleeve was used with two zippers, i.e. the same as Test Sleeve 3 Zippers but with one gusset/secondary zipper. This test sleeve ("Test Sleeve 2 Zippers") with both zippers open had in a non-stretched state the same dimensions at the Test Sleeve 3 Zippers.

A reference example using a sleeve corresponding to the test sleeves but without gussets and secondary zippers was conducted. This reference sleeve ("Reference 1 Zipper") with its main zipper open had in a non-stretched state the same dimensions at the test sleeves.

Using a spring scale attached to zipper sliders, the forces to close the aforesaid sleeves on an adult lower leg have a circumference of 42 cm at the widest part of the calf were measured. For the Reference 1 Zipper, the main zipper was opened, the sleeve was then placed around the lower leg in the supine position and then the main zipper was closed, again in the supine position. For the Test Sleeve 2 Zippers, the main zipper and the secondary zipper were opened, the sleeve was then placed around the lower leg, the main zipper was closed, and then the secondary zipper was closed, again all in the supine position. When the main zipper of the Test Sleeve 2 Zippers was closed, but the secondary zipper was still open, the width at the lower edge was 29 cm, the width at the upper edge was 41 cm, and at the widest position of the calf (i.e. 10 cm from the upper edge) the width was 42 cm, all measurements determined using a measuring tape, on the outside of the sleeve. For the Test Sleeve 3 Zippers, the main zipper and the two secondary zippers were opened, the sleeve was then placed around the lower leg, the main zipper was closed, then one of secondary zipper was closed and finally the other secondary zipper was closed, all done in the supine position. When the main zipper of this test sleeve was closed, but the two secondary zippers were still open, the width at the lower edge was 30 cm, the width at the upper edge was 41 cm, and at the widest position of the calf (i.e. 10 cm from the upper edge) the width was 43 cm, all measurements determined using a measuring tape, on the outside of the sleeve. The speed used to close the zippers represented a typical, average speed for zipper-closing procedure. The tests were repeated two times. The results are summarized in the following table (average values).

| | Maximal closing force (N) | | |
| --- | --- | --- | --- |
| Test Specimen | Main zipper | First secondary zipper | Second secondary zipper |
| Reference 1 zipper | 36 | not applicable | not applicable |
| Test Sleeve 2 Zippers | 20 | 18 | not applicable |
| Test Sleeve 3 Zippers | 8 | 10 | 16 |

The highest closing force, 20 N, measured for the Test Sleeve 2 Zippers is nearly half of that measured for the reference, 36 N that, while the highest closing force measured for the Test Sleeve 3 Zippers, 16 N, is less than half of that measured for the reference. The supine and standing pressures exerted onto the calf by all the sleeves were measured and found to be equivalent for each position, 18 and 48 N, respectively.

The invention claimed is:

1. A compression device for applying compression to a body part of a user comprising a sleeve for substantially covering a portion of the body part of a user, wherein the sleeve has an upper edge, a lower edge and an opening extending from the sleeve's upper edge to the sleeve's lower edge, said opening having two side edges, wherein the first side edge is provided with one half of a main zipper and the second side edge is provided with a complementary half of said main zipper, wherein the sleeve includes at least one expandable gusset provided with a releasable closure system extending along the length of said gusset, said gusset and releasable closure system being configured and arranged, such that when said releasable closure system is closed said gusset is prevented from expansion and when said releasable closure system is opened said gusset is allowed to expand between the opened parts of the releasable closure system so as to allow for an expansion of the width of the sleeve.

2. A compression device according to claim 1, wherein the sleeve comprises two sub-components, a first sub-component including the first half of the main zipper and the second sub-component including the second half of the main zipper, wherein the two sub-components are releasably attached to one another and positioned in series along the transverse direction of the sleeve.

3. A compression device according to claim 2, wherein the first and second sub-components of the sleeve are releasably attached to one another using a tertiary releasable closure system.

4. A compression device according to claim 3, wherein said tertiary releasable closure system is a mechanical fastening closure system, wherein the interior surface of at least the portion of the second sub-component that is near or adjacent to lateral edge of the second sub-component is provided with hook, stem and/or cup-shaped fasteners and the exterior surface of at least the portion of the first sub-component that is near or adjacent to lateral edge of first sub-component has a structure or is provided with a structure that is adapted to be engaged by said fasteners.

5. A compression device according to claim 4, wherein the releasably attached first and second sub-components overlap and/or wherein first and second sub-components are configured and arranged such that the extent of overlap can be adjusted and/or the lateral edge portion of the first sub-component is trimmable.

6. A compression device according to claim 1, wherein in use on said body part of the user the sleeve is disposed about a central axis (A), said central axis lying in a plane (P).

7. A compression device according to claim 6, wherein in use on said body part of the user and when said main zipper and releasable closure system are closed, the releasable closure system extends along a second axis (B), wherein relative to a projection of the second axis onto said plane (P) containing the central axis (A), the second axis is either in parallel alignment or inclined forming an acute angle ($\beta$) up to 45° inclusive relative to the central axis.

8. A compression device according to claim 1, wherein the main zipper is a separating-type zipper.

9. A compression device according to claim 8, wherein the sleeve comprises a main part for substantially covering a main portion of the body part, said main part extending from the second side edge of the sleeve towards to the first side edge, and wherein the exterior surface of the main part is provided with two or more separating zipper halves positioned in series along the transverse direction of the sleeve, each of said two or more separating zipper halves extending from the upper edge and to lower edge of the sleeve and each being complementary to the half of the main zipper provided on the first side edge.

10. A method of applying a compression device according to claim 1 onto the body part on a user, said method comprising the steps of:
   a) opening the main zipper and opening the at least one expandable gusset by opening the gusset's releasable closure system;
   b) positioning the sleeve about the body part of the user;
   c) closing the main zipper; and
   d) closing the gusset-associated releasable closure system, whereby if sleeve includes two or more gussets the closure of the releasable closure systems may be performed, as applicable, sequentially or simultaneously.

11. A method according to claim 10, wherein the sleeve comprises two sub-components, a first sub-component including the first half of the main zipper and the second sub-component including the second half of the main zipper, wherein the two sub-components are releasably attached to one another and positioned in series along the transverse direction of the sleeve, and wherein the method comprises the step of releasably attaching the first and second sub-components together, said step to be performed prior to step a).

12. A compression device according to claim 1, wherein said at least one gusset is substantially rectangular in shape; triangular in shape; diamond-shaped; canoe-shaped or rowboat-shaped.

13. A compression device according to claim 1, wherein said at least one gusset is made of a material having elasticity in at least the transverse direction of the sleeve.

14. A compression device according to claim 1, wherein said at least one gusset is made of a material that does not have elasticity in at least the transverse direction of the sleeve and wherein said gusset and the gusset's associated releasable closure system are configured and arranged such that when the releasable closure system is closed the gusset folds up behind the releasable closure system and when the releasable closure system is opened, said gusset can unfold between the opened parts of the releasable closure system.

15. A compression device according to claim 1, wherein the sleeve includes two or more expandable gussets, each provided with a releasable closure system.

16. A compression device according to claim 1, wherein said releasable closure system is a secondary zipper, in particular a non-separating type zipper.

* * * * *